(12) United States Patent
Thompson et al.

(10) Patent No.: US 9,079,885 B2
(45) Date of Patent: Jul. 14, 2015

(54) FLUORESCENT ISOINDOLINE DYES

(75) Inventors: Mark E. Thompson, Anaheim, CA (US); Kenneth Hanson, Los Angeles, CA (US); Peter Djurovich, Long Beach, CA (US)

(73) Assignee: The University of Southern California, Los Angeles, CA (US)

( * ) Notice: Subject to any disclaimer, the term of this patent is extended or adjusted under 35 U.S.C. 154(b) by 635 days.

(21) Appl. No.: 13/316,901

(22) Filed: Dec. 12, 2011

(65) Prior Publication Data

US 2012/0153266 A1 Jun. 21, 2012

Related U.S. Application Data

(60) Provisional application No. 61/423,822, filed on Dec. 16, 2010.

(51) Int. Cl.
| | |
|---|---|
| *H01L 51/54* | (2006.01) |
| *C07D 401/14* | (2006.01) |
| *C07D 209/40* | (2006.01) |
| *C07D 209/44* | (2006.01) |
| *H01L 51/50* | (2006.01) |
| *H01L 51/00* | (2006.01) |
| *C09K 11/06* | (2006.01) |

(52) U.S. Cl.
CPC .............. *C07D 401/14* (2013.01); *C07D 209/44* (2013.01); *C09K 11/06* (2013.01); *C09K 2211/1018* (2013.01); *C09K 2211/18* (2013.01); *H01L 51/0072* (2013.01); *H01L 51/0077* (2013.01); *H01L 51/5012* (2013.01)

(58) Field of Classification Search
None
See application file for complete search history.

(56) References Cited

U.S. PATENT DOCUMENTS

| | | | | |
|---|---|---|---|---|
| 2004/0169461 | A1* | 9/2004 | Moriyama et al. | 313/503 |
| 2009/0243468 | A1* | 10/2009 | Thompson et al. | 313/504 |

FOREIGN PATENT DOCUMENTS

JP       59185349 A  * 10/1984

OTHER PUBLICATIONS

Park et al. J. Am. Chem. Soc. 2009, 131, 14043-14049. Date of web publication: May 29, 2009.*

* cited by examiner

*Primary Examiner* — Andrew K Bohaty
(74) *Attorney, Agent, or Firm* — Morgan, Lewis & Bockius, LLP

(57) ABSTRACT

The present invention provides a new class of excited state intramolecular charge transfer (ESIPT) dye compounds based on mono or dihydroxy substituted 1,3-bisiminoisoindole motif and metal complexes containing such compounds as ligands. The present invention also provides OLEDs containing the compound and/or metal complex as the emissive material.

3 Claims, 10 Drawing Sheets

Figure 9. Room-temperature absorption spectra of a) 1, b) 2, c) 3, d) 4 e) 5 and f) 6 in toluene, CH$_2$Cl$_2$ and methanol.

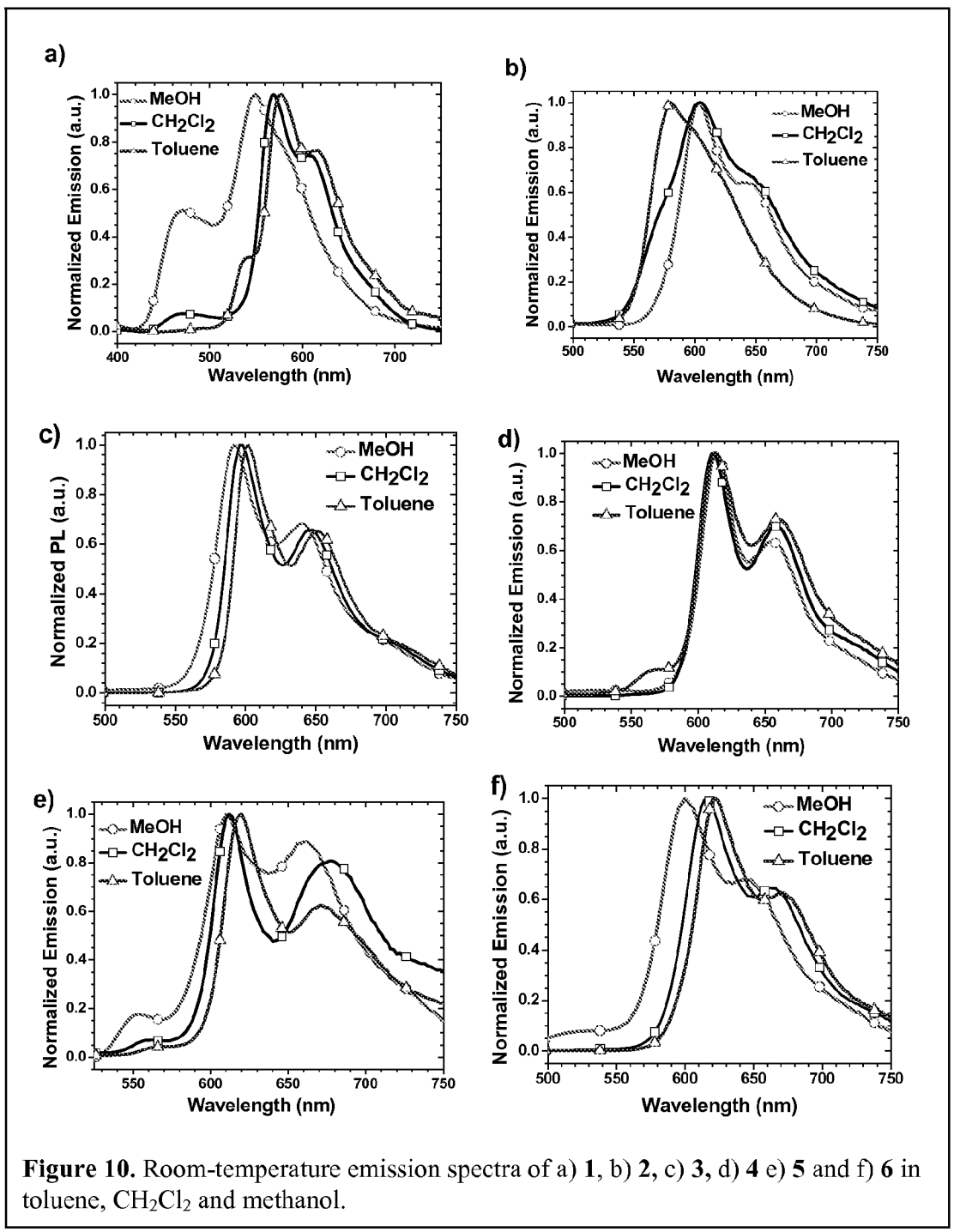
Figure 10. Room-temperature emission spectra of a) 1, b) 2, c) 3, d) 4 e) 5 and f) 6 in toluene, $CH_2Cl_2$ and methanol.

FLUORESCENT ISOINDOLINE DYES

REFERENCE TO RELATED APPLICATIONS

This application claims priority to U.S. Provisional Application No. 61/423,822, filed Dec. 16, 2010, the content of which is incorporated herein by reference in its entirety.

RESEARCH AGREEMENTS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to a new class of excited state intramolecular charge transfer (ESIPT) dye compounds based on mono or dihydroxy substituted 1,3-bisiminoisoindole motif and metal complexes containing such compounds as ligands. The present invention also relates to uses of these compounds and/or metal complexes in organic light emitting devices.

BACKGROUND OF THE INVENTION

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted $Ir(ppy)_3$, which has the structure of Formula I:

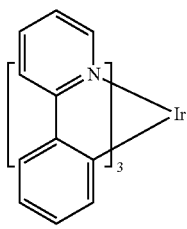

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule", and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

1,3-bis(2-pyridylimino)isoindoline (BPI) was originally synthesized in 1952 in two steps, as described by Elvidge, J. A.; Linstead, R. P. *J. Chem. Soc.* 1952, 5000, and later one step as described by Clark, P. F.; Elvidge, J. A.; Linstead, R. P. *J. Chem. Soc.* 1953, 3593, both of which are incorporated herein by reference. The production of gram scale quantities required harsh reaction conditions and as a result, produced many side reactions including formation of phthalocyanine and related chromophoric by-products. It was not until the metal ion catalyzed reaction (Scheme 1) published by Siegl in 1977 (Siegl, W. O. *J. Org. Chem.* 1977, 42, 1872-1878, incorporated herein by reference) that the BPI ligand became a viable option for various applications. The BPI ligand is interesting for many types of research because it is easy to prepare, is highly stable and can be easily modified to suit a particular interest. Examples of this include Siegl's later work (see Siegl, W. O. *J. Heterocycl. Chem.* 1981, 18, 1613) producing water soluble derivatives; BPI derivatives capable of chelating two, e.g., described in Siegl, W. O. *Inorg. Chem. Acta* 1977, 25, L65, or even three, e.g., described in Marks, D. N.; Siegl, W. O.; Gangne, R. R. *Inorg. Chem.* 1982, 21, 3140-3147, and Anderson, O. P.; la Cour, A. Dodd, A.; Garrett, A. D.; Wicholas, M. *Inorg. Chem.* 2003, 42, 1.22-127, metal ions; and derivatives with extended conjugation, e.g., described in Baird, D. M.; Maehlmann, W. P.; Bereman, R. D.; Singh, P. *J. Coord. Chem.* 1997, 42, 107-126, all of which are incorporated herein by reference.

Scheme 1. Standard reaction conditions
for the synthesis of BPI and realted compounds.

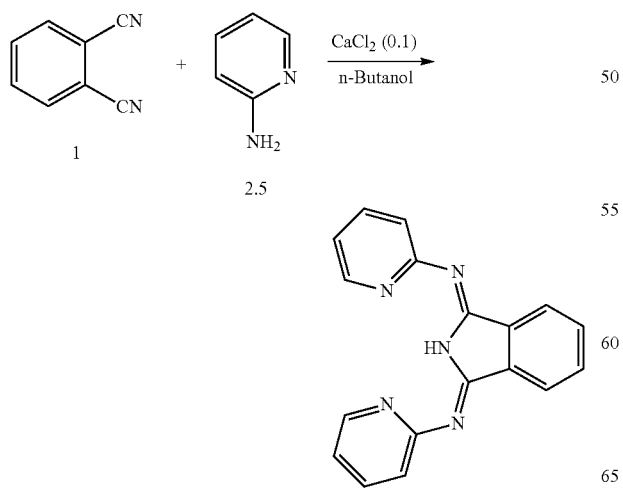

SUMMARY OF THE INVENTION

The present invention provides an excited state intramolecular charge transfer (ESIPT) dye compound based on mono or dihydroxy substituted 1,3-bisiminoisoindole motif and a metal complex containing such a compound as ligand.

In one embodiment, the present invention provides a compound of the following formula:

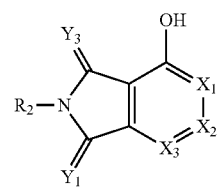

wherein $Y_1$ and $Y_3$ are independently S, O, or $NR_1$, and S, O, or $NR_3$, respectively, with at least one of $Y_1$ and $Y_3$ being $NR_1$ and $NR_3$, respectively, $R_1$ and $R_3$ each being an atom or a functional group, wherein $R_1$ and $R_3$ can optionally form a ring; $R_2$ is an atom or a functional group, wherein $R_2$ can optionally form a ring with $Y_1$ and/or form a ring with $Y_3$; and $X_1$, $X_2$, and $X_3$ are independently N or $CR_4$, N or $CR_5$, and N or $CR_6$, respectively, $R_4$, $R_5$, and $R_6$ each being an atom or a functional group, wherein $R_4$ and $R_5$ and/or $R_5$ and $R_6$ can optionally form a ring or $R_4$ and $R_6$ can optionally form a ring.

In another embodiment, the present invention provides a complex comprising a metal atom M and a ligand as shown by the following formula:

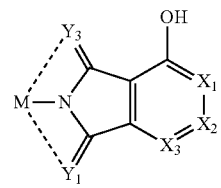

wherein - - - - - represents an optional coordination bond, at least one of which being present and wherein $Y_1$ and $Y_3$ are independently S, O, or $NR_1$, and S, O, or $NR_3$, respectively, with at least one of $Y_1$ and $Y_3$ being $NR_1$ and $NR_3$, respectively, $R_1$ and $R_3$ each being an atom or a functional group, at least one containing an atom for forming a coordination bond, wherein $R_1$ and $R_3$ can optionally form a ring; and $X_1$, $X_2$, and $X_3$ are independently N or $CR_4$, N or $CR_5$, and N or $CR_6$, respectively, $R_4$, $R_5$, and $R_6$ each being an atom or a functional group, wherein $R_4$ and $R_5$ and/or $R_5$ and $R_6$ can optionally form a ring or $R_4$ and $R_6$ can optionally form a ring. The metal M can be a transition metal or a lanthanide.

In yet another embodiment, the present invention provides an OLED comprising an organic layer disposed between an anode and a cathode, where the organic layer comprises the compound and/or the metal complex of the present invention.

BRIEF DESCRIPTION OF THE DRAWINGS

FIG. 10 shows the emission spectra of Compounds (1)-(6).

DETAILED DESCRIPTION OF THE INVENTION

Figure 1:
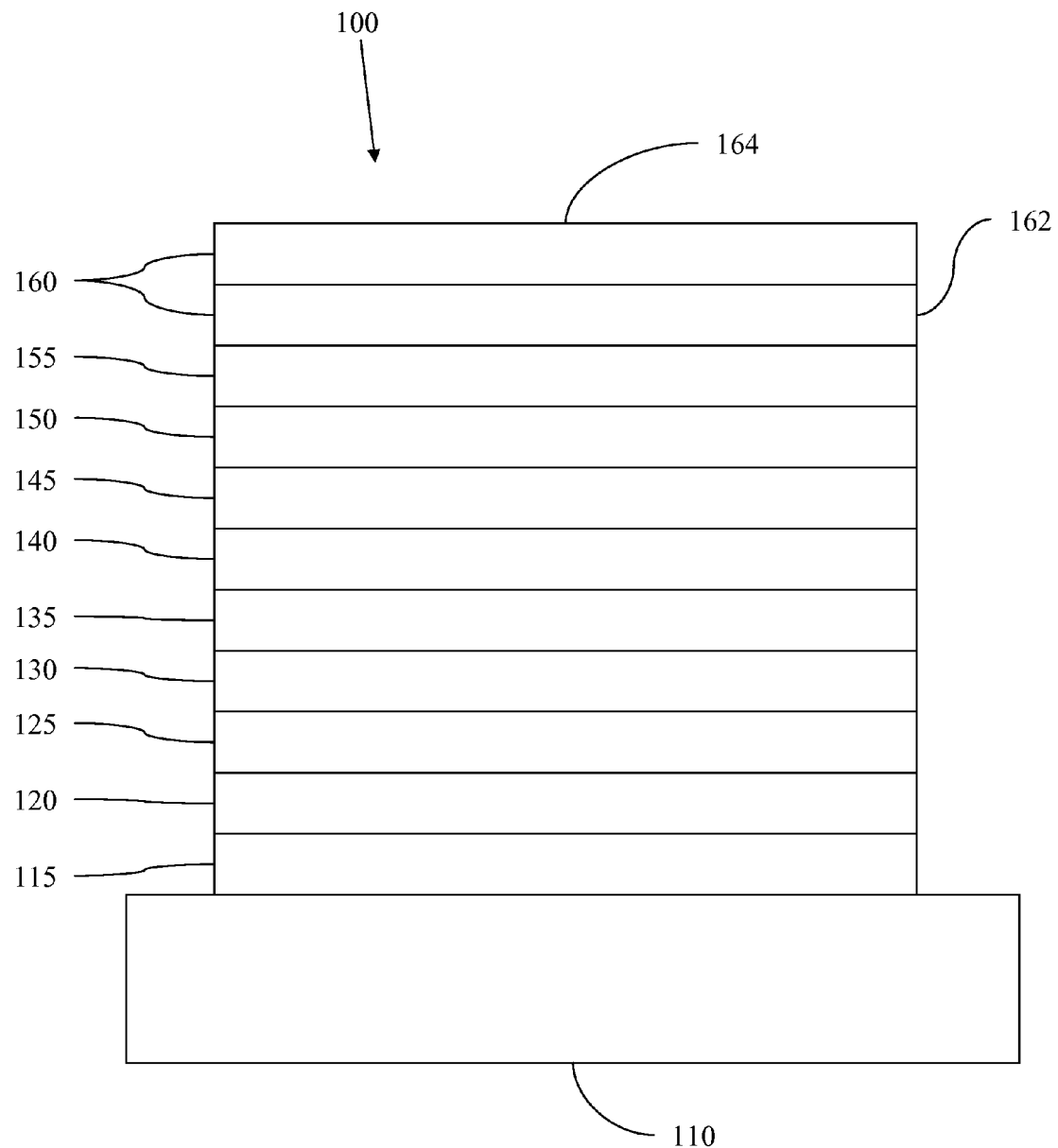
FIG. 1 shows an organic light emitting device.

The present invention provides a new class of ESIPT dye molecules based on mono or dihydroxy substituted 1,3-bisiminoisoindole motif. The invention is based, at least in part, on the discovery that mono or dihydroxy substituted BPI exhibits several of the characteristics common to excited state intramolecular charge transfer (ESIPT) molecules. The ESIPT nature of such a compound was confirmed by both the lack of emission from the alkoxy substituted BPI and the large changes in lifetime/efficiency in deuterated methanol (MeOD). Although ESIPT emission has been observed for similar compounds (IE hydroxyphthalimide based ESIPT dyes), as described in Wakita, J.; Inoue, S.; Kawanishi, N.; Ando, S. *Macromolecules* 2010, 43 (8), 3594-3605, Sultanova, Nina; Staneva, T. *Proc. Of SPIE* 2003, 5226, 99-103, Gruzinsky, V. V.; and Staneva, T. G. *Zh. Prikl. Spektr.* 1975, 23 (5), 820-827, all of which are incorporated herein by reference; the mono or dihydroxy substituted 1,3-bisiminoisoindole motif in the compound of the invention offers one important advantage, two readily modifiable substitutents not present in phthalimide.

In one embodiment, the invention provides a compound of the following formula (I):

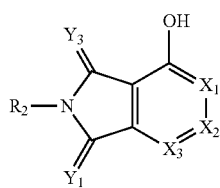

(I)

wherein $Y_1$ and $Y_3$ are independently S, O, or $NR_1$, and S, O, or $NR_3$, respectively, with at least one of $Y_1$ and $Y_3$ being $NR_1$ and $NR_3$, respectively, $R_1$ and $R_3$ each being an atom or a functional group, wherein $R_1$ and $R_3$ can optionally form a ring; $R_2$ is an atom or a functional group, wherein $R_2$ can optionally form a ring with $Y_1$ and/or form a ring with $Y_3$; and $X_1$, $X_2$, and $X_3$ are independently N or $CR_4$, N or $CR_5$, and N or $CR_6$, respectively, $R_4$, $R_5$, and $R_6$ each being an atom or a functional group, wherein $R_4$ and $R_5$ and/or $R_5$ and $R_6$ can optionally form a ring or $R_4$ and $R_6$ can optionally form a ring.

Typically, $R_1$, $R_2$, and $R_3$ are independently selected from the group consisting of H, a halogen, a hydroxy group, an amino group, a carboxyl group, an aliphatic group, a heteroaliphatic group, a cyclic group, a heterocyclic group, an aromatic group, a heteroaromatic group, and a combination thereof. The combination includes, but not limited to, an aliphatic aromatic group, an aliphatic heteroaromatic group; an aliphatic cyclic group, and an aliphatic heterocyclic group. The heteroaliphatic group includes, but not limited to, an aliphatic amine, an aliphatic acid, an aliphatic ketone, an aliphatic alkoxy, and an aliphatic ester. In one embodiment, $R_1$, $R_2$, and/or $R_3$ is an alkyl, cycloalkyl, alkenyl, alkynyl, aryl, heteroaryl, or aralkyl.

Typically, $R_4$, $R_5$, and $R_6$ are independently selected from the group consisting of H, a halogen, a hydroxy group, an amino group, a carboxyl group, an aliphatic group, a heteroaliphatic group, a cyclic group, a heterocyclic group, an aromatic group, a heteroaromatic group, and a combination thereof. The combination includes, but not limited to, an aliphatic aromatic group, an aliphatic heteroaromatic group; an aliphatic cyclic group, and an aliphatic heterocyclic group. The heteroaliphatic group includes, but not limited to, an aliphatic amine, an aliphatic acid, an aliphatic ketone, an aliphatic alkoxy, and an aliphatic ester. In one embodiment, $R_4$, $R_5$, and/or $R_6$ is an alkyl, cycloalkyl, alkenyl, alkynyl, aryl, heteroaryl, or aralkyl.

In a preferred embodiment, the invention provides dye molecules as shown in Scheme 2 below.

Scheme 2. Examples of fluorescent
ESIPT dye molecules of the present invention.

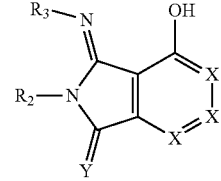

a)

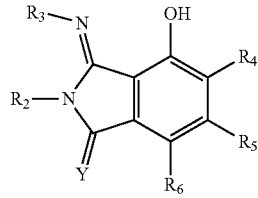

b)

$Y = S, O$ or $NR_1$

The compounds of the invention can be categorized according to the location of substitution. Below is a list of some categories containing a brief summary and several examples of each.

In one embodiment, $Y_1$ is $NR_1$. In another embodiment, $Y_3$ is $NR_3$. In still another embodiment, $Y_1$ is $NR_1$ and $Y_3$ is $NR_3$. $R_1$, $R_2$, and $R_3$ can be any atom (including H) or group. Additionally, $R_1$, $R_2$, and $R_3$ can all be the same or different groups depending on the synthetic method used. Examples of possible hydrocarbon groups at $R_1$, $R_2$, or $R_3$ are shown in Scheme 3. Examples of other possible groups are shown in Scheme 4.

Scheme 3. Examples of possible hydrocarbon
groups at $R_{1-3}$, shown with the N atom to which the
group is attached, where n can be any number of $CH_2$ groups.

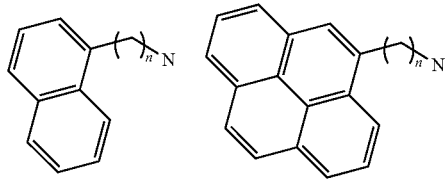

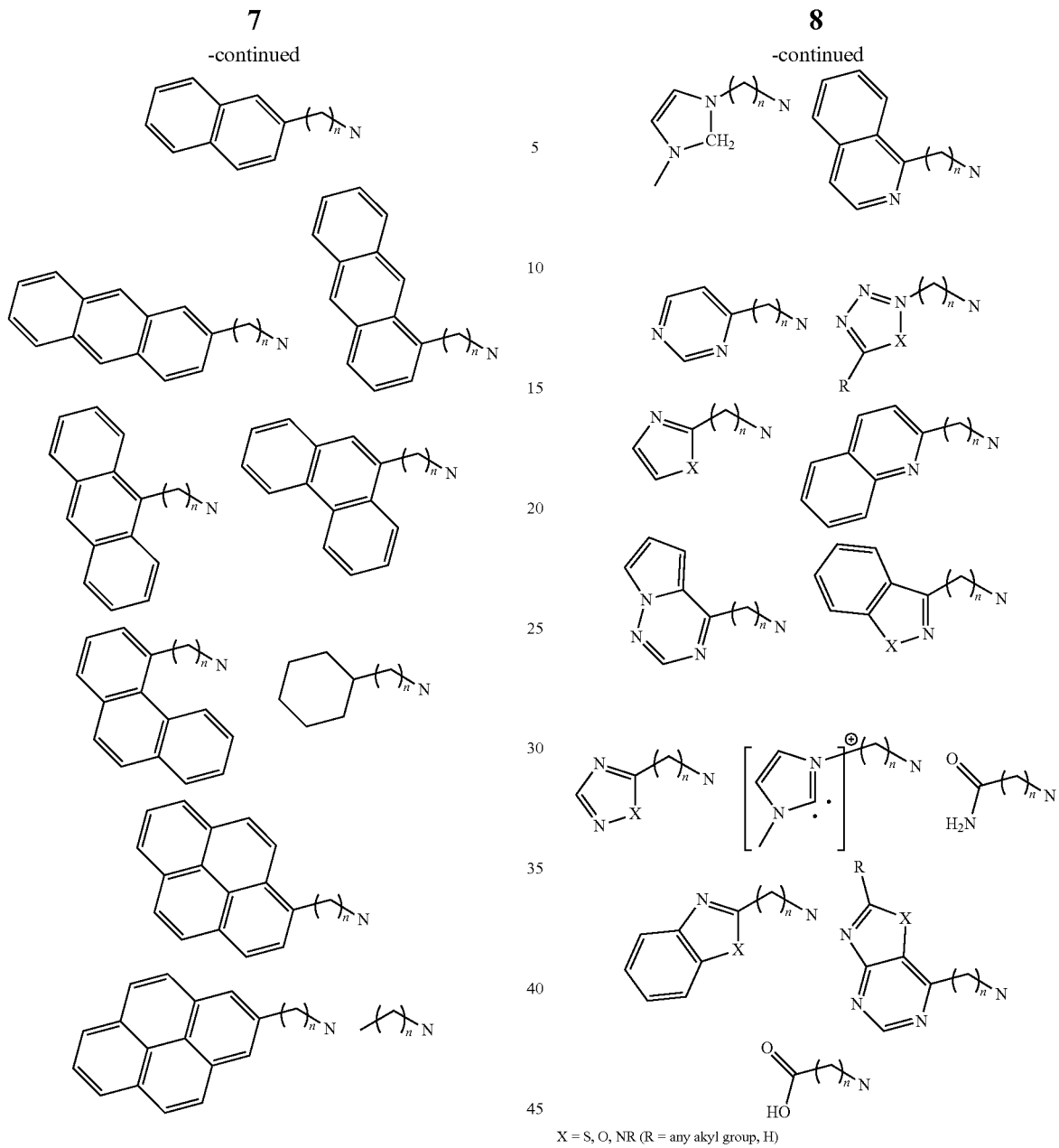

X = S, O, NR (R = any akyl group, H)

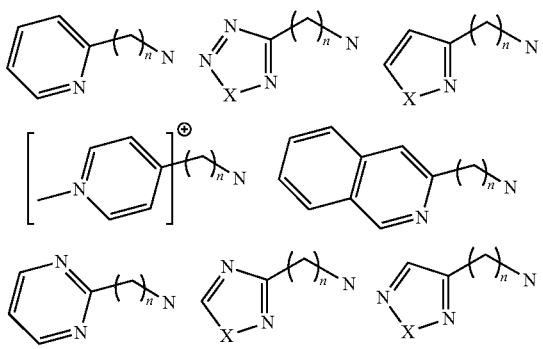

Scheme 4. Examples of other possible groups at $R_{1-3}$, shown with the N atom to which the group is attached, where n can be any number of $CH_2$ groups.

In addition to the possible independent substituents at $R_1$, $R_2$ and $R_3$, connections at $R_1$ and $R_2$, $R_2$ and $R_3$, and $R_1$ and $R_3$ are possible. Thus, in one embodiment, $R_2$ and $R_3$ together form a ring. In another embodiment, $R_1$ and $R_2$ together form a ring. In still another embodiment, $R_1$ and $R_3$ together form a ring. This category also contains any molecules with extended conjugation at position $R_1$ and $R_2$ and/or $R_2$ and $R_3$. Any of the extended moieties can be added at $R_1$ and $R_2$ and/or $R_2$ and $R_3$. In another embodiment, rings formed at both $R_1$ and $R_2$ and $R_2$ and $R_3$ and fused together.

In one embodiment, $R_2$ and $R_3$ or $R_1$ and $R_2$ together form a six membered ring bridging $R_2$ and $R_3$ or $R_1$ and $R_2$ with —CH=CH—. In a preferred embodiment, $R_1$ and $R_2$ or $R_2$ and $R_3$ together form a ring selected from the group consisting of phenylene, naphthalene, anthracene, and heterocyclic analogs of the same.

Examples of this type of structure are shown in Scheme 5.

Scheme 5. Examples of molecules with substituents
connected at position $R_{1,2}$, $R_{1,3}$ and $R_{2,3}$
where n can be any number of repeating units.

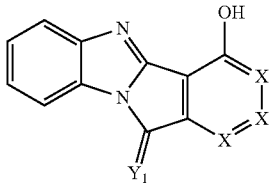

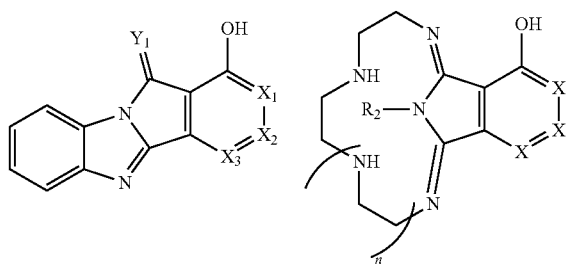

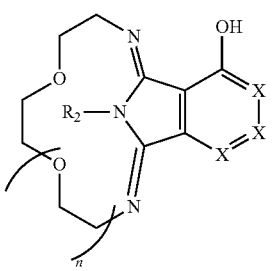

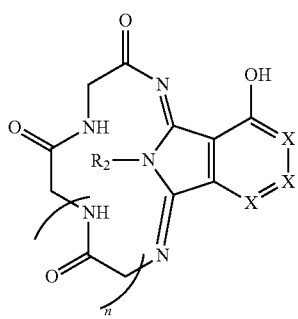

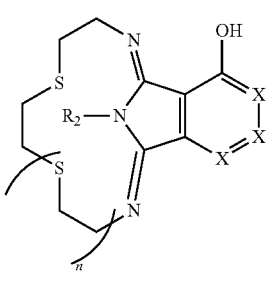

In another embodiment, the invention provides a compound of the following formula:

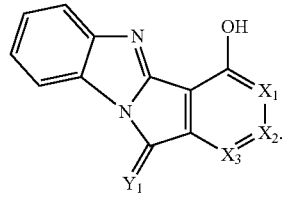

This is an example of the compound wherein $R_2$ and $R_3$ together form a ring.

In another embodiment, the invention provides a compound of the following formula:

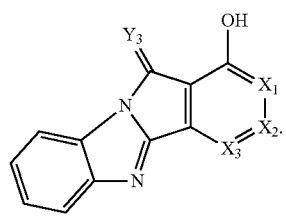

This is an example of the compound wherein $R_1$ and $R_2$ together form a ring.

$R_4$, $R_5$, and $R_6$ can be any atom (including H) or group. Additionally, $R_{4-6}$ can all be the same or different groups. In a preferred embodiment, $X_3$ is $CR_6$, where $R_6$ is a hydroxy group. In another embodiment, $X_1$ is $CR_4$, $X_2$ is $CR_5$, and $X_3$ is $CR_6$.

In one embodiment, $R_4$ and $R_5$ together form a ring or $R_5$ and $R_6$ together form a ring. In another embodiment, $R_4$ and $R_6$ together form a ring. This category also contains any molecules with extended conjugation at position $R_4$ and $R_5$ and/or $R_5$ and $R_6$. Any of the extended moieties can be added at $R_4$ and $R_5$ and/or $R_5$ and $R_6$. In another embodiment, rings formed at both $R_4$ and $R_5$ and $R_5$ and $R_6$ and fused together. Examples of these compounds are shown in Scheme 6.

Scheme 6. Examples of molecules with extended
conjugation at position $R_{4,5}$ and $R_{5,6}$ where X
can be N, CH or CR and Y can be S, O, NH or NR.

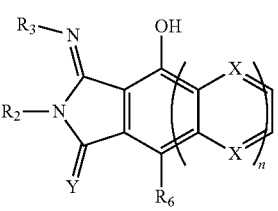

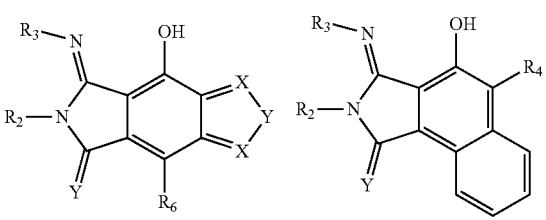

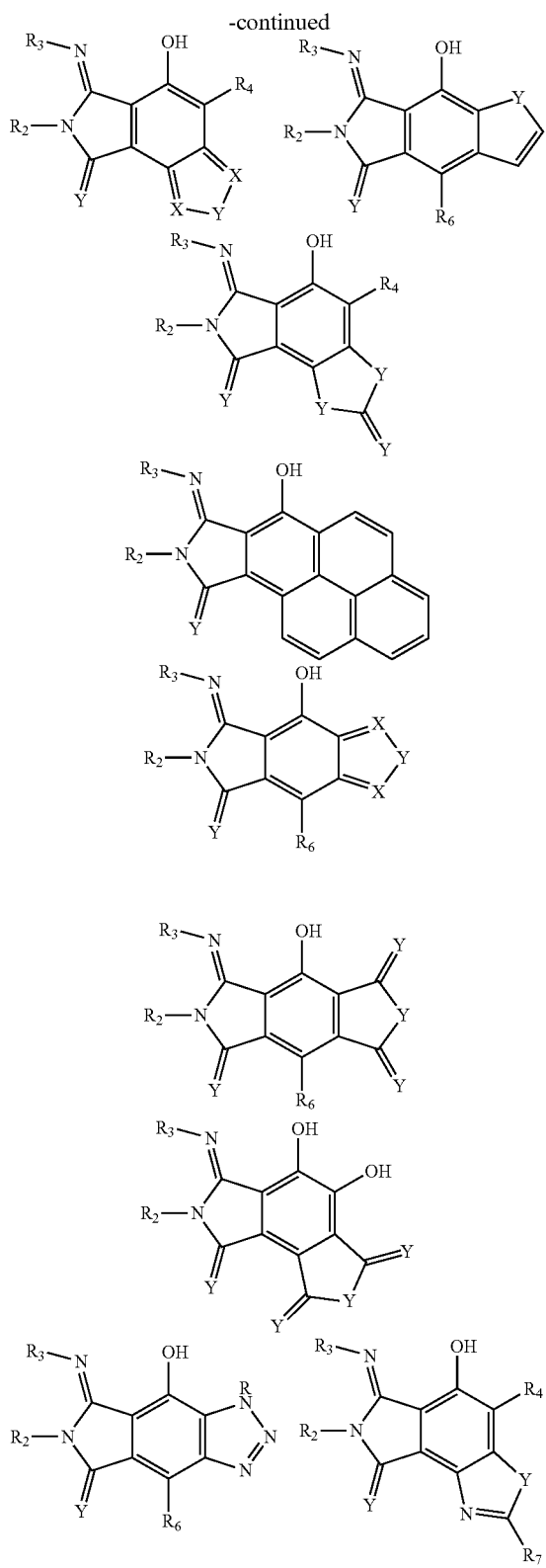

In another embodiment, $R_4$ and $R_5$ or $R_5$ and $R_6$ together form a six membered ring bridging $R_4$ and $R_5$ or $R_5$ and $R_6$ with —CH=CH—. In a preferred embodiment, $R_4$ and $R_5$ or $R_5$ and $R_6$ together form a ring selected from the group consisting of phenylene, naphthalene, anthracene, and heterocyclic analogs of the same.

In a specific embodiment, the invention provides a compound of formula (I) in which $Y_1$ and $Y_3$ are $NR_1$ and $NR_3$, respectively, $R_1$ and $R_3$ being the same functional group selected from the group consisting of $C_{12}H_{25}$, 4-tBu-Ph, 2-pyridyl, and 1-isoquinolyl; $R_2$ is H; $X_1$ and $X_2$ are $CR_4$ and $CR_5$, respectively, $R_4$ and $R_5$ being OH or Cl, and $X_3$ is $CR_6$, $R_6$ being OH or OEt.

The invention also provides metal complexes containing any of the aforementioned compounds as ligands coordinated to a metal center (either transition metal or lanthanide). Preferably, the compound coordinates to the metal center as either a tridentate or bidentate ligand. In a similar manner multiple ligands can be coordinated to a single metal center. In one embodiment, the metal complex contains two or more ligands, at least one of which is a compound of the invention.

In one embodiment, the invention provides a complex comprising a metal atom M and a ligand as shown by the following formula (II):

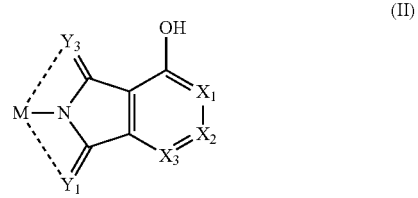

(II)

wherein - - - - - represents an optional coordination bond, preferably at least one of which being present, and wherein $Y_1$ and $Y_3$ are independently S, O, or $NR_1$, and S, O, or $NR_3$, respectively, with at least one of $Y_1$ and $Y_3$ being $NR_1$ and $NR_3$, respectively, $R_1$ and $R_3$ each being an atom or a functional group, at least one containing an atom for forming a coordination bond, wherein $R_1$ and $R_3$ can optionally form a ring; and $X_1$, $X_2$, and $X_3$ are independently N or $CR_4$, N or $CR_5$, and N or $CR_6$, respectively, $R_4$, $R_5$, and $R_6$ each being an atom or a functional group, wherein $R_4$ and $R_5$ and/or $R_5$ and $R_6$ can optionally form a ring or $R_4$ and $R_6$ can optionally form a ring.

In one embodiment, $Y_3$ is $NR_3$, where $R_3$ is a functional group containing an atom for forming a coordination bond. In another embodiment, $Y_1$ is $NR_1$, where $R_1$ is a functional group containing an atom for forming a coordination bond. In still another embodiment, $R_1$ and/or $R_3$ is a functional group comprising a nitrogen which forms a coordination bond with M.

The metal M can be a transition metal or a lanthanide. In one embodiment, M is a third row transition metal. In a specific embodiment, M is Ir, Pt, Re, or Os. In another embodiment, M is a second row transition metal. In a specific embodiment, M is Pd, Rh, or Ru. In another specific embodiment, M is La, Ce, Nd, or Eu.

In a specific embodiment, $Y_1$ and $Y_3$ are $NR_1$ and $NR_3$, respectively, $R_1$ and $R_3$ being the same functional group selected from the group consisting of 2-pyridyl, and 1-isoquinolyl; $X_1$ and $X_2$ are $CR_4$ and $CR_5$, respectively, $R_4$ and $R_5$ being OH or Cl, and $X_3$ is $CR_6$, $R_6$ being OH or OEt.

In one embodiment, the invention provides the following metal complexes containing an ESIPT molecule of the invention as a ligand.

Scheme 7. Examples of metal complexes containing ESIPT molecules of the invention as ligands

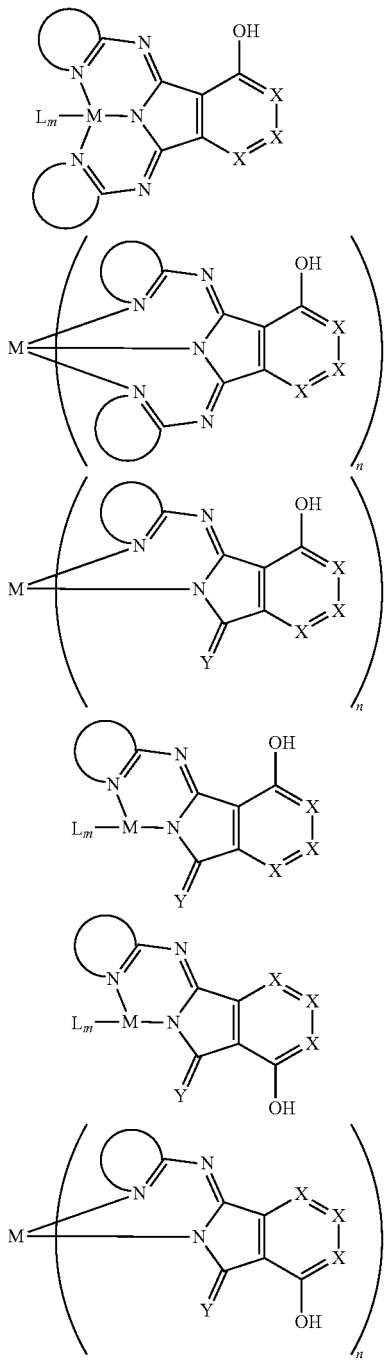

wherein ◯ represents an optional ring, L represents a ligand, where m and n represent the number of respective ligands, e.g., m=1, 2, 3, 4, 5, 6, or more, and n=1, 2, 3, 4, or more.

The compounds of the invention with readily variable structure can be synthesized by any method known in the art. The photophysical properties of the compounds of the invention can be tuned through substitution. The compounds exhibit relatively high efficiencies ($\Phi > 0.20$) and molar absorptivities ($\epsilon > 1 \times 10^4$ M$^{-1}$ cm$^{-1}$), making these dyes ideal candidates for many applications including, but not limited to, laser dyes (see, e.g., Chou, P.; McMorrow, D.; Aartsma, T. J.; Kasha, M. *J. Phys. Chem.* 1984, 88, 4596-4599), fluorescent probes (see, e.g., Sytnik, A.; Del Valle, J. C. *J. Phys. Chem.* 1995, 99, 13028-13032), photostabilizers (see, e.g., Chou, P. T.; Martinez, M. L. *Radiat. Phys. Chem.* 1993, 41, 373-378), and high energy radiation detectors (see, e.g., Stein, M.; Keck, J.; Waiblinger, F.; Fluegge, A. P.; Kramer, H. E. A.; Hartschuh, A.; Port, H.; Leppard, D.; Rytz, G. *J. Phys. Chem. A*, 2002, 106, 2055-2066), all of which are incorporated herein by reference.

In one embodiment, the invention provides an OLED containing the compound and/or the metal complex of the invention as the emissive material. The compound and/or the metal complex of the invention can be included in one or more emissive layers of the OLED. In one embodiment, the compound and/or the metal complex of the invention is included in the emissive layer as a dopant in a host material, e.g., a host material disclosed hereinbelow. In another embodiment, the compound and/or the metal complex of the invention is used in an OLED in combination with a phosphorescent material, e.g., a phosphorescent material disclosed hereinbelow.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton", which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference. The compound and/or the metal complex of the invention can be used in OLEDs in combination with a phosphorescent material, e.g., in the same emissive layer or in separate emissive layers.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
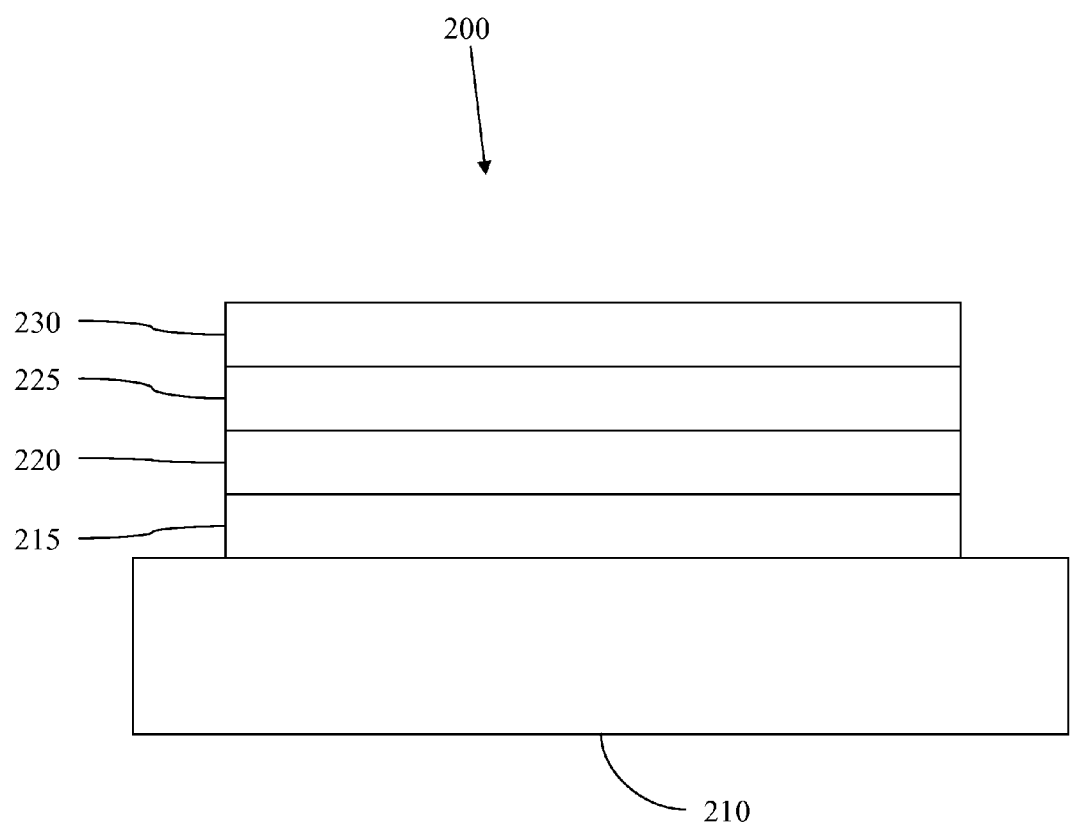
FIG. 2 shows an inverted organic light emitting device that does not have a separate electron transport layer.
Figure 3:
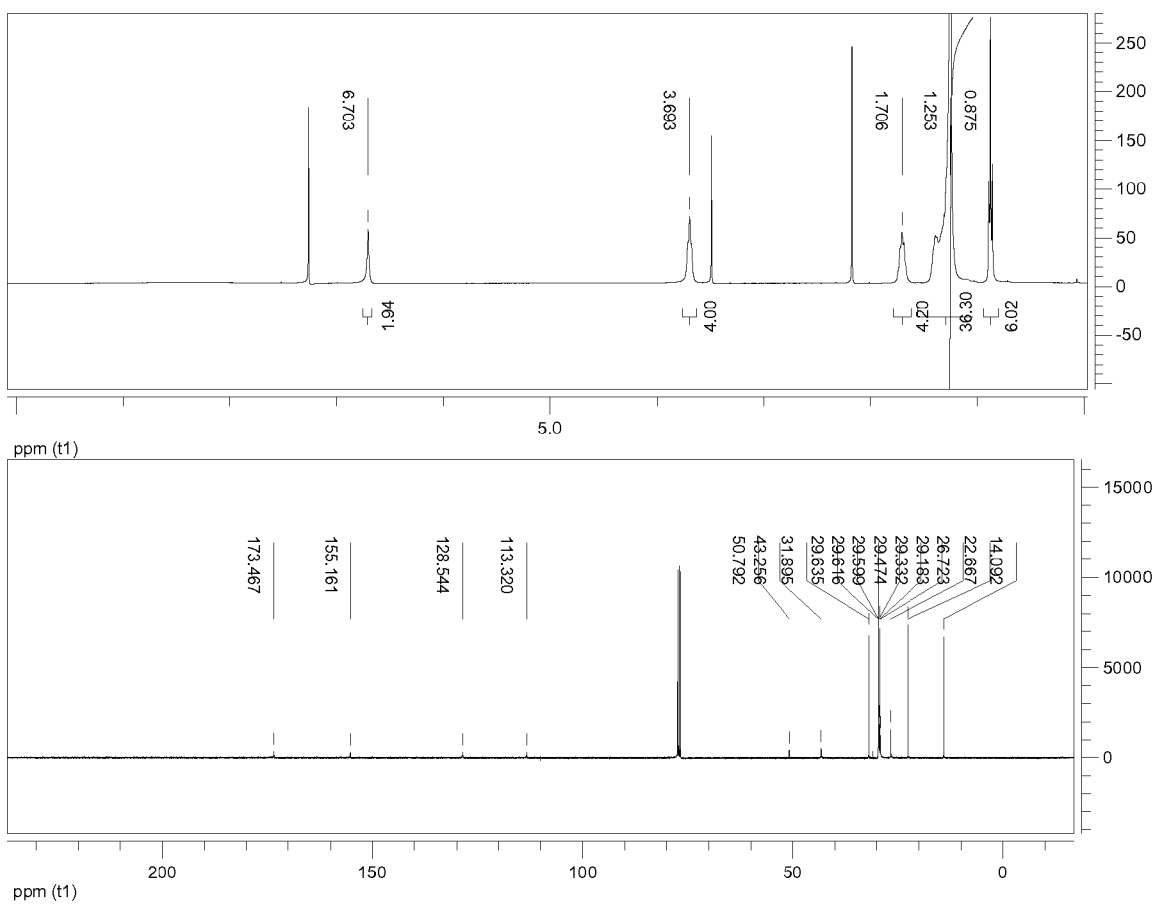
FIG. 3 shows an $^1H$ NMR and $^{13}C$ NMR spectra for 1,3-bis(dodecylimino)-4,7-dihydroxyisoindole (1).
Figure 4:
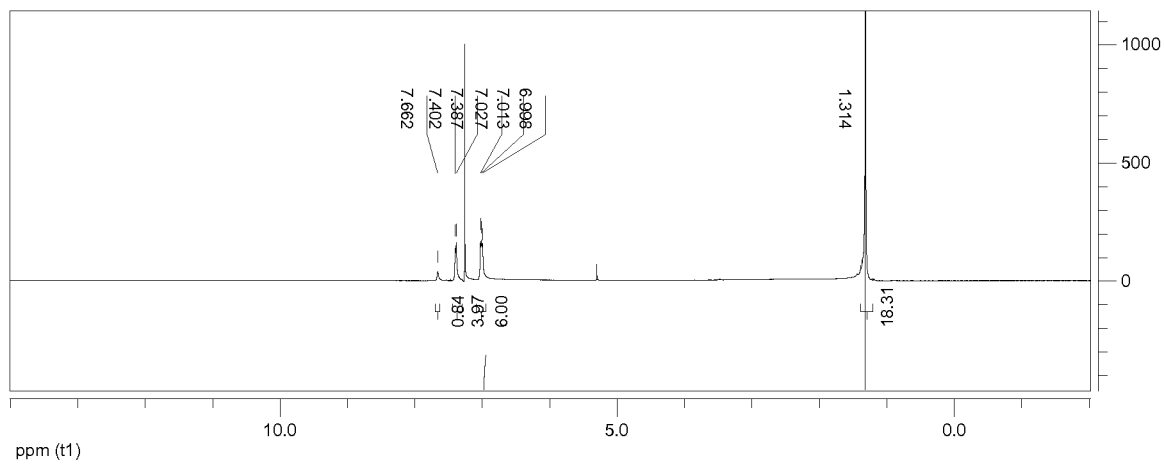
FIG. 4 shows an $^1$H NMR spectra for 1,3-bis(p-tert-butyl-phenylimino)-4,7-dihydroxyisoindole (2).
Figure 5:
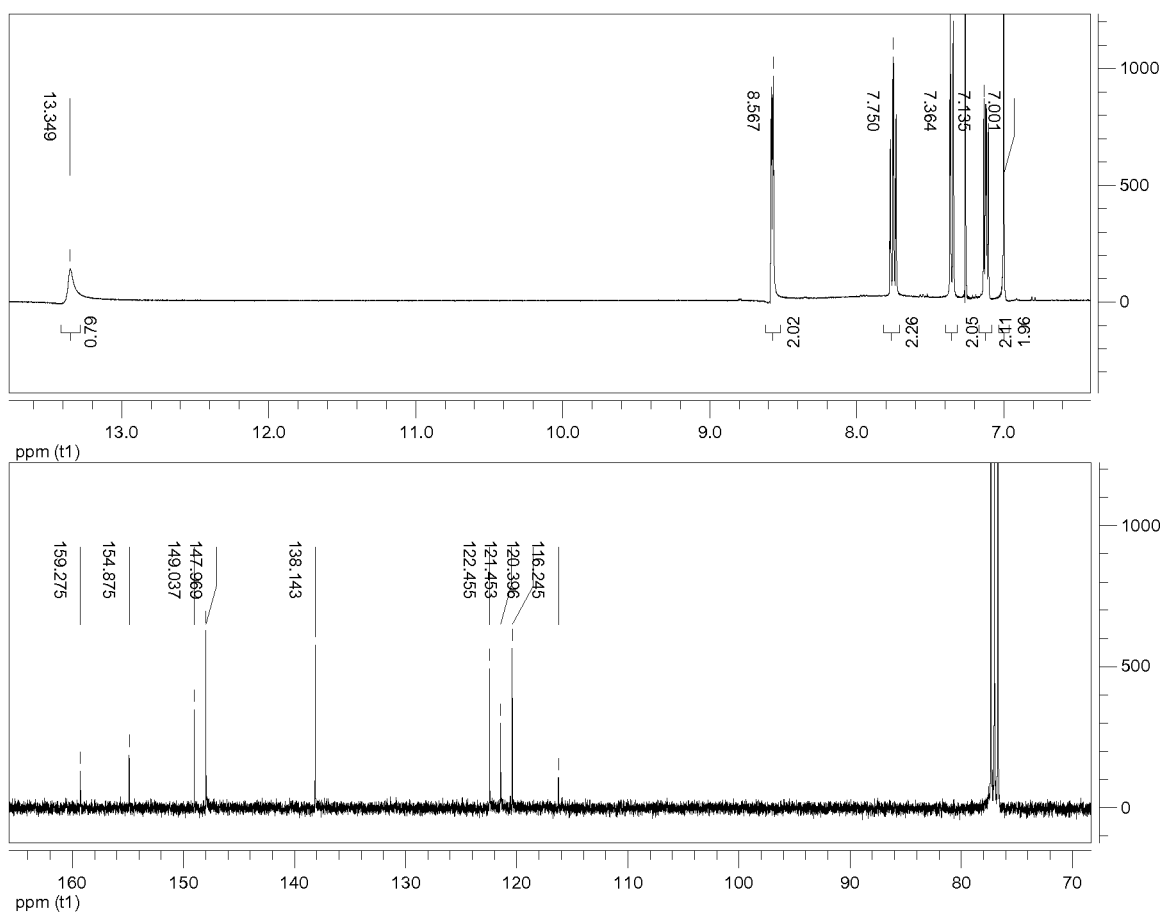
FIG. 5 shows an $^1$H NMR and $^{13}$C NMR spectra for 1,3-bis(2-pyridylimino)-4,7-dihydroxyisoindole (3).
Figure 6:
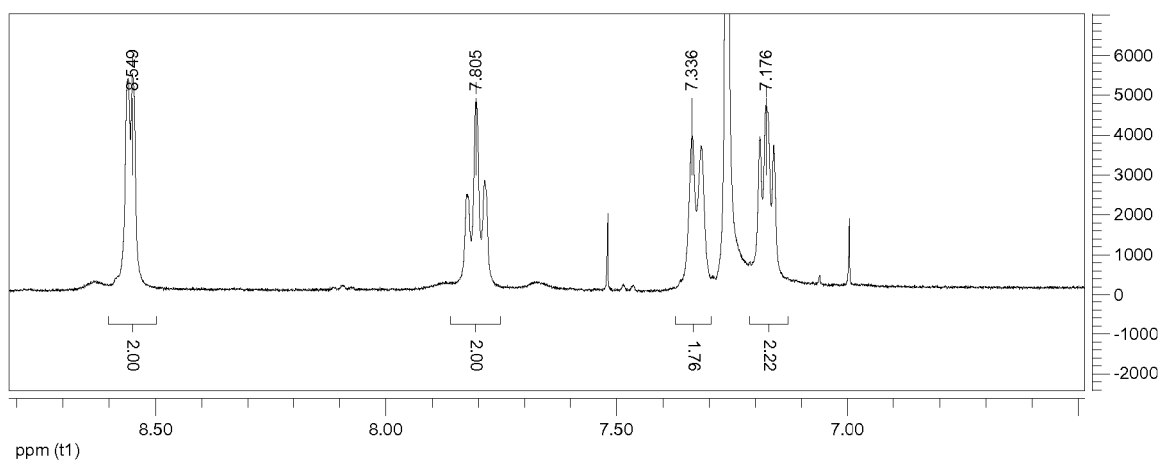
FIG. 6 shows an $^1$H NMR spectra for 5,6-dichloro-1,3-bis (2-pyridylimino)-4,7-dihydroxyisoindole (4).
Figure 7:
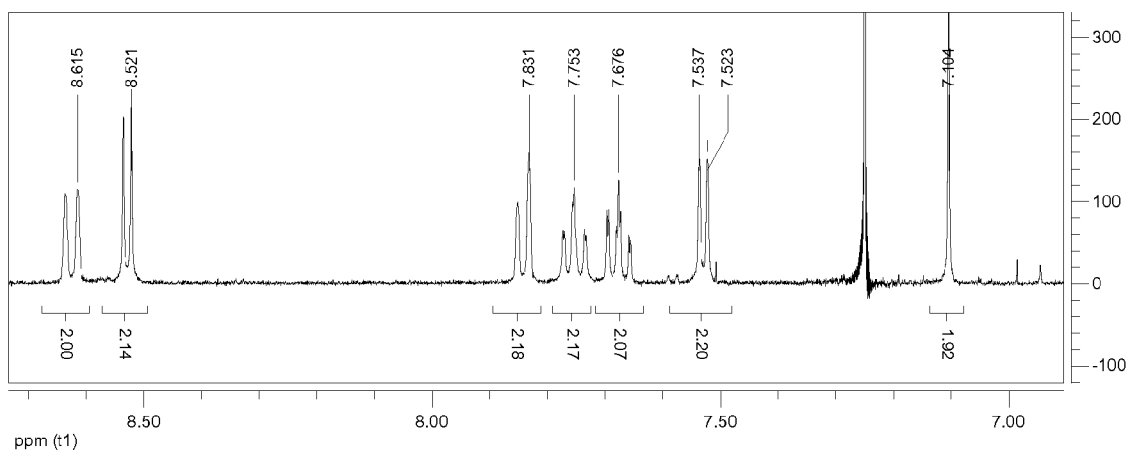
FIG. 7 shows an $^1$H NMR spectra for 1,3-bis(1-isoquinolylimino)-4,7-dihydroxyisoindole (5).
Figure 8:
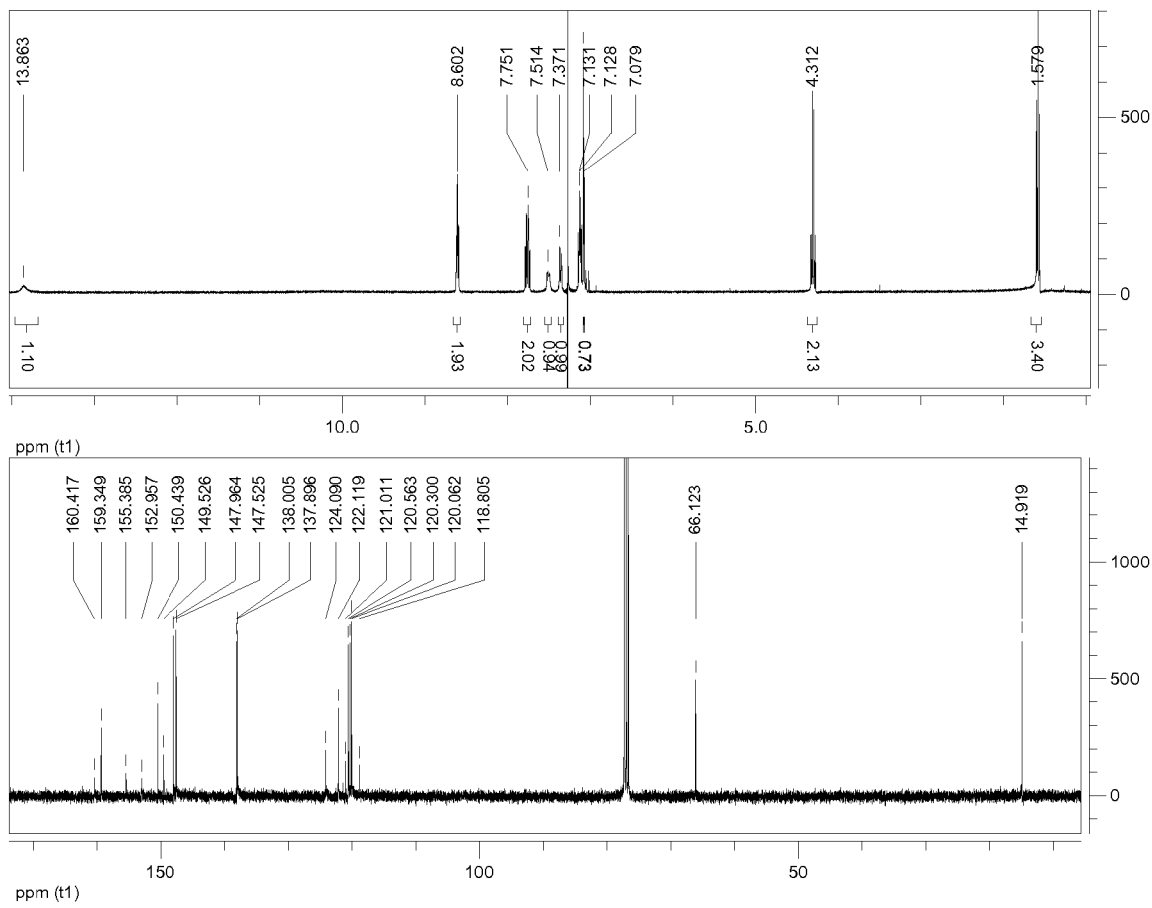
FIG. 8 shows an $^1$H NMR and $^{13}$C NMR spectra for 1,3-bis(2-pyridylimino)-4-ethoxy-7-hydroxyisoindole (6).

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18° C. to 30° C., and more preferably at room temperature (20-25° C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined below.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR, wherein each R is independently selected from H, alkyl, alkenyl, alkynyl, aralkyl, aryl and heteroaryl.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "alkynyl" as used herein contemplates both straight and branched chain alkyne radicals. Preferred alkyl groups are those containing two to fifteen carbon atoms.

Additionally, the alkynyl group may be optionally substituted with one or more substituents selected from halo, CN, $CO_2R$, C(O)R, $NR_2$, cyclic-amino, $NO_2$, and OR.

The terms "aralkyl" as used herein contemplates an alkyl group that has as a substituent an aromatic group. Additionally, the aralkyl group may be optionally substituted on the aryl with one or more substituents selected from halo, CN, $CO_2R$, C(O)R, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted with one or more substituents selected from halo, CN, $CO_2R$, C(O)R, $NR_2$, cyclic-amino, $NO_2$, and OR.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls. Additionally, the aryl group may be optionally substituted with one or more substituents selected from halo, CN, $CO_2R$, C(O)R, $NR_2$, cyclic-amino, $NO_2$, and OR.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Additionally, the heteroaryl group may be optionally substituted with one or more substituents selected from halo, CN, $CO_2R$, C(O)R, $NR_2$, cyclic-amino, $NO_2$, and OR.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
|---|---|---|
| Starburst triarylamines | 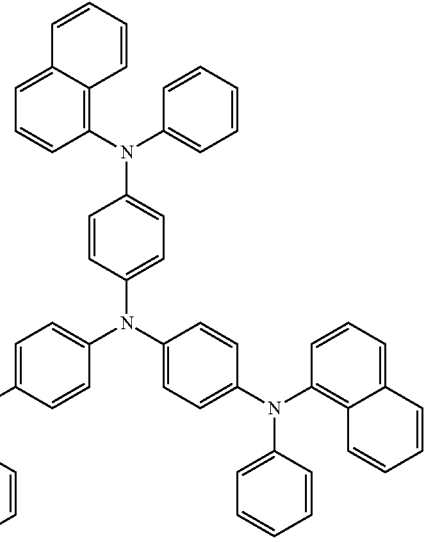 | J. Lumin. 72-74, 985 (1997) |
| CF$_x$ Fluorohydrocarbon polymer | 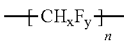 | Appl. Phys. Lett. 78, 673 (2001) |
| Conducting polymers (e.g., PEDOT:PSS, polyaniline, polypthiophene) | 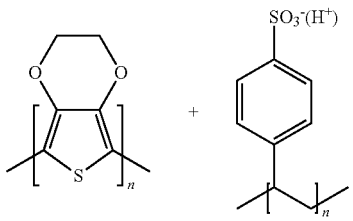 | Synth. Met. 87, 171 (1997) |
| Arylamines complexed with metal oxides such as molybdenum and tungsten oxides | 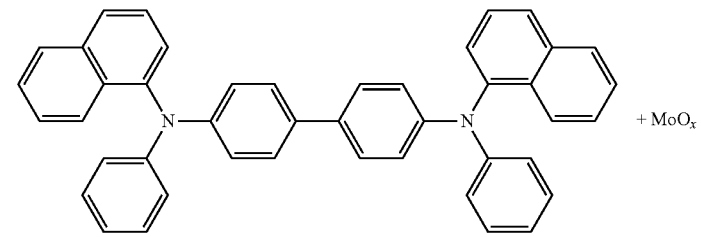 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) |
| Hole transporting materials | | |
| Triarylamines (e.g., TPD, α-NPD) | 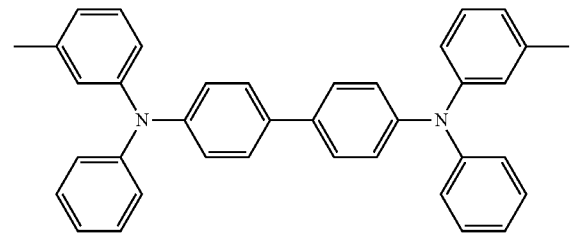 | Appl. Phys. Lett. 51, 913 (1987) |

| MATE-RIAL | EXAMPLES OF MATERIAL | PUBLI-CATIONS |
|---|---|---|
| | 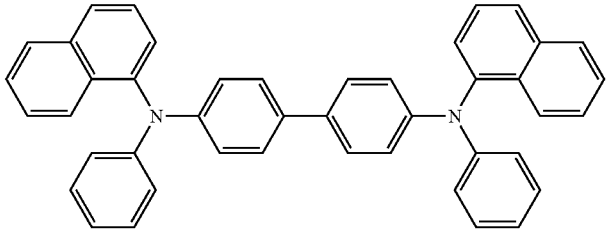 [SMILES: c1ccc(N(c2ccc(-c3ccc(N(c4ccccc4)c4cccc5ccccc45)cc3)cc2)c2cccc3ccccc23)cc1] | US5061569 |
| | 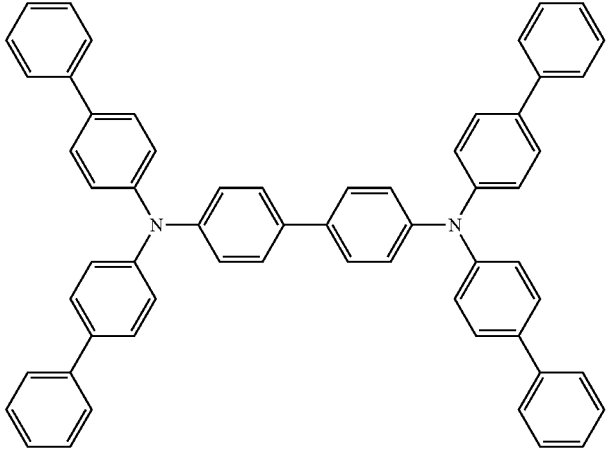 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 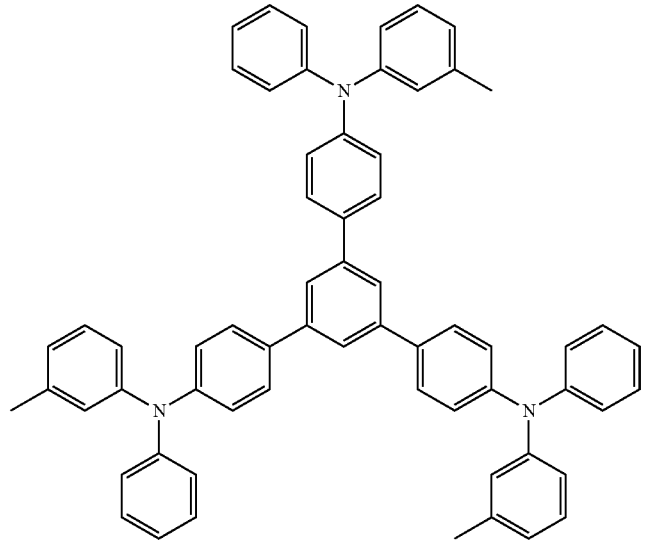 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued
| MATERIAL | EXAMPLES OF MATERIAL | PUBLICATIONS |
|---|---|---|
| | 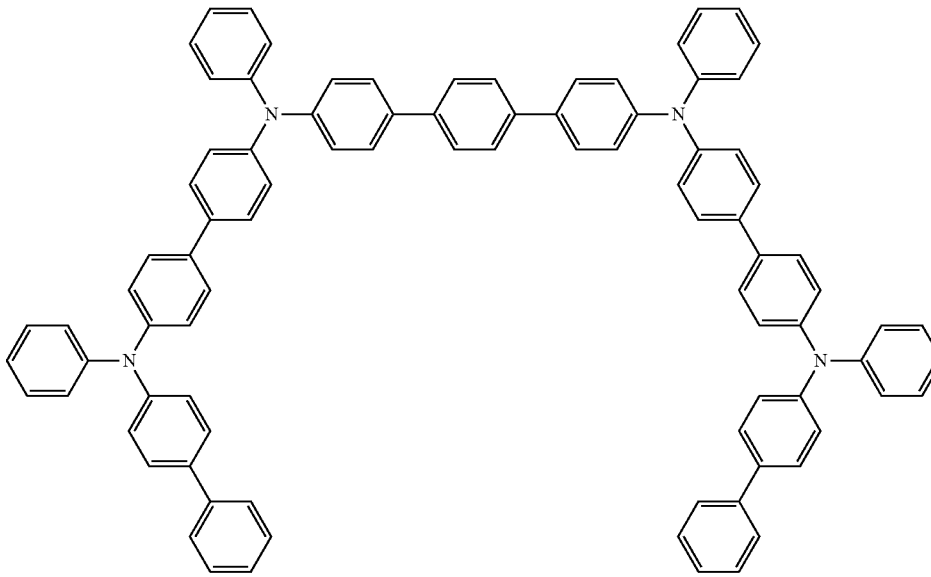 | Appl. Phys. Lett. 90, 183503 (2007) |
| | 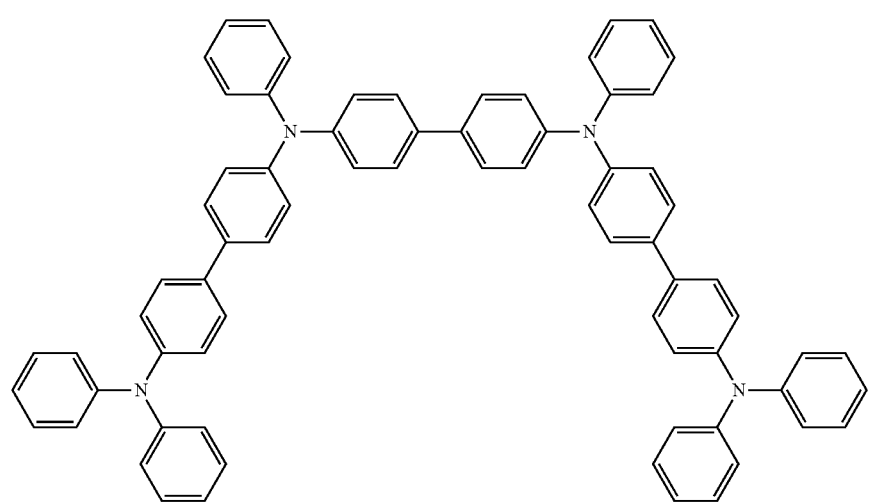 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spiro-fluorene core | 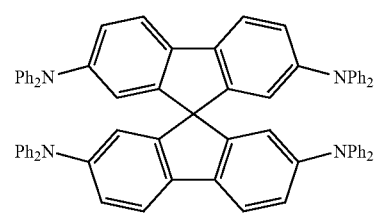 | Synth. Met. 91, 209 (1997) |

TABLE 1-continued
| MATERIAL | EXAMPLES OF MATERIAL | PUBLICATIONS |
|---|---|---|
| Arylamine carbozle compounds | 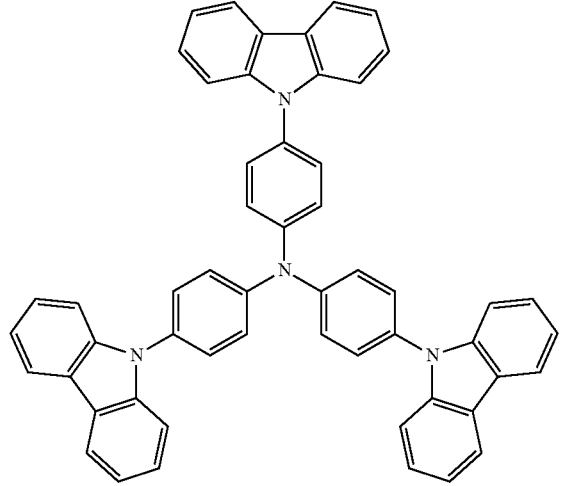 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994) |
| Indolocarbazoles | 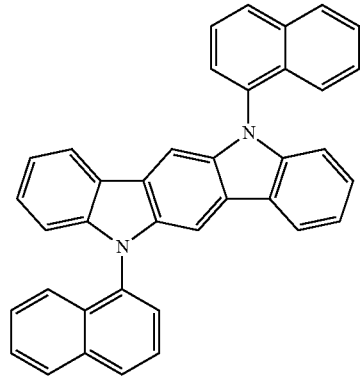 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 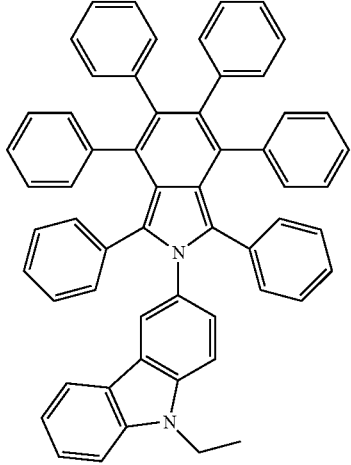 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
Phosphorescent OLED host materials

TABLE 1-continued
| MATERIAL | EXAMPLES OF MATERIAL | PUBLICATIONS |
|---|---|---|
| Red hosts | | |
| Arylcarbazoles | 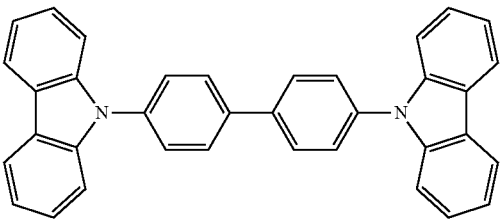 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e. g., Alq$_3$, BAlq) | 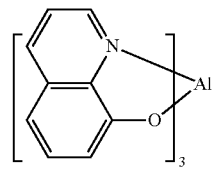 | Nature 395, 151 (1998) |
| | 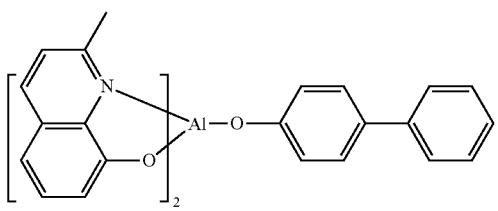 | US20060202194 |
| | 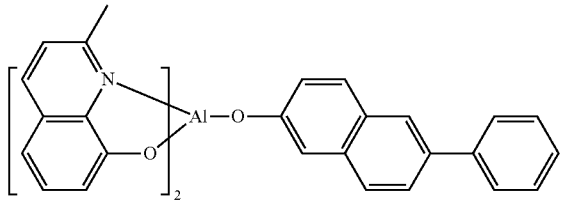 | WO2005014551 |
| Metal phenoxybenzothiazole compounds | 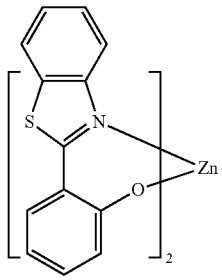 | Appl. Phys. Lett. 90, 123509 (2007) |
| Conjugated oligomers and polymers (e. g., polyfluorene) | 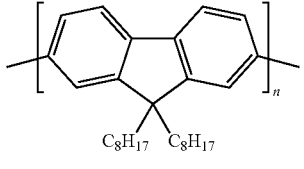 | Org. Electron. 1, 15 (2000) |
| Green hosts | | |

TABLE 1-continued
| MATERIAL | EXAMPLES OF MATERIAL | PUBLICATIONS |
|---|---|---|
| Arylcarbazoles | 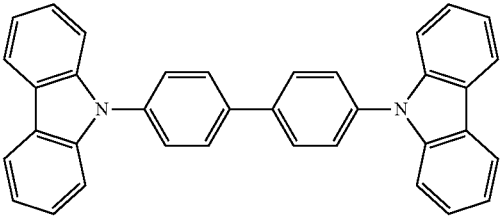 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
|  | 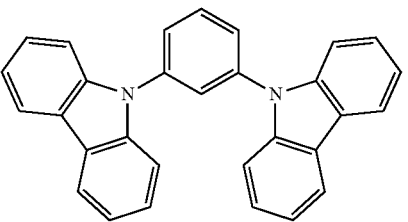 [SMILES: c1cc(-n2c3ccccc3c3ccccc32)cc(-n2c3ccccc3c3ccccc32)c1] | US2003175553 |
|  | 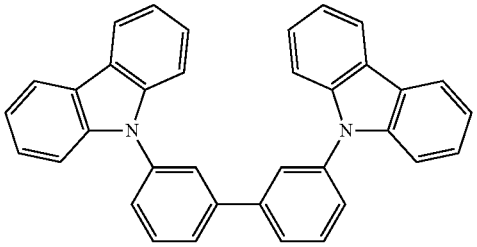 [SMILES: c1cc(-c2cccc(-n3c4ccccc4c4ccccc43)c2)cc(-n2c3ccccc3c3ccccc32)c1] | WO2001039234 |
| Aryltriphenylene compounds | 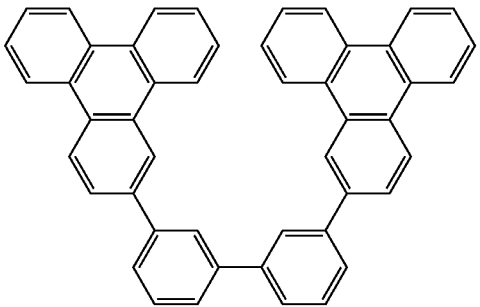 [SMILES: c1cc(-c2cccc(-c3ccc4c5ccccc5c5ccccc5c4c3)c2)cc(-c2ccc3c4ccccc4c4ccccc4c3c2)c1] | US20060280965 |
|  | 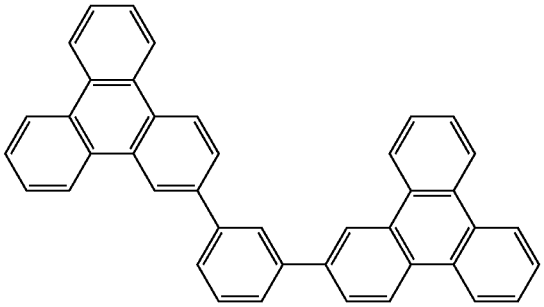 [SMILES: c1cc(-c2ccc3c4ccccc4c4ccccc4c3c2)cc(-c2ccc3c4ccccc4c4ccccc4c3c2)c1] | US20060280965 |
| Polymers (e.g., PVK) | 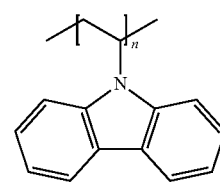 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 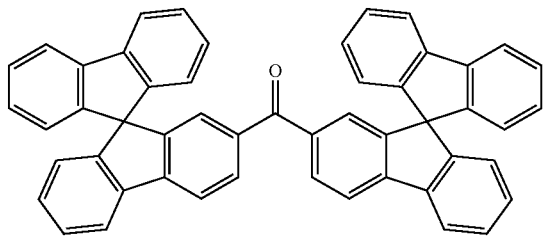 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 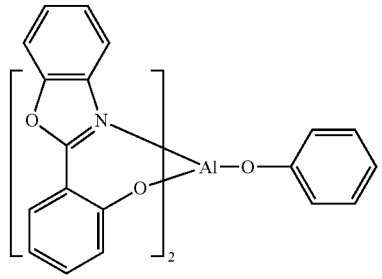 | WO05089025 |
| | 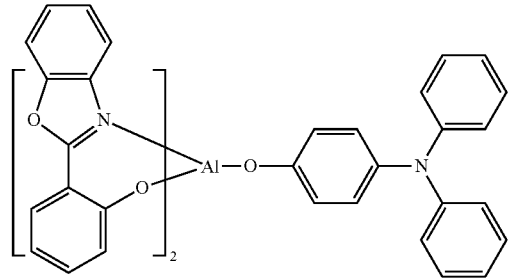 | WO06132173 |
| | 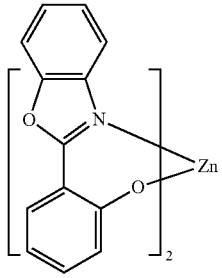 | JP200511610 |
| Spirofluorene-carbazole compounds | 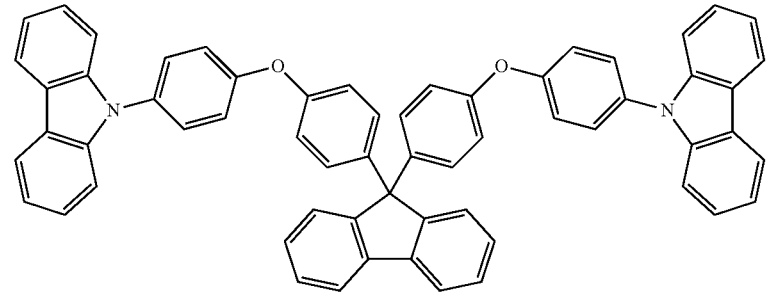 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 1-continued

| MATERIAL | EXAMPLES OF MATERIAL | PUBLICATIONS |
|---|---|---|
| | | JP2007254297 |
| Idolocabazoles | | WO07063796 |
| | | WO07063754 |
| 5-member ring electron deficient heterocycles (e. g., triazole, oxadiazole) | | J. Appl. Phys. 90, 5048 (2001) |
| | | WO04107822 |

TABLE 1-continued

| MATERIAL | EXAMPLES OF MATERIAL | PUBLICATIONS |
|---|---|---|
| Metal phenoxypyridine compounds | | WO05030900 |
| Blue hosts | | |
| Arylcarbazoles | | Appl. Phys. Lett. 82, 2422 (2003) |
| | | US20070190359 |
| Dibenzothiophenecarbazole compounds | | WO2006114966 |

Phosphorescent dopants

Red dopants

| | | |
|---|---|---|
| Heavy metal porphyrins (e. g., PtOEP) | | Nature 395, 151 (1998) |

TABLE 1-continued

| MATERIAL | EXAMPLES OF MATERIAL | PUBLICATIONS |
|---|---|---|
| Iridium (III) organometallic complexes | | Appl. Phys. Lett. 78, 1622 (2001) |
| | | US06835469 |
| | | US06835469 |
| | | US20060202194 |
| | | US20060202194 |

| MATE-RIAL | EXAMPLES OF MATERIAL | PUBLI-CATIONS |
|---|---|---|
| | [Ir complex with methyl-substituted benzo[h]quinoline ligand]$_3$ | US07087321 |
| | [Ir complex with phenylisoquinoline ligand]$_3$ | US07087321 |
| | [Ir complex with octyl-substituted phenylisoquinoline ligand]$_3$ (H$_{17}$C$_8$) | Adv. Mater. 19, 739 (2007) |
| Platinum (II) organo-metallic complexes | Pt complex with phenylisoquinoline and acetylacetonate ligands | WO2003040257 |
| Osminum (III) complexes | Os(PPhMe$_2$)$_2$ complex with CF$_3$-pyrazolyl-pyridine ligand | Chem. Mater. 17, 3532 (2005) |
| Ruthe-nium (II) complexes | [Ru(PPhMe$_2$)$_2$ complex with $^t$Bu-pyrazolyl-isoquinoline ligand]$_2$ | Adv. Mater. 17, 1059 (2005) |

TABLE 1-continued
| MATERIAL | EXAMPLES OF MATERIAL | PUBLICATIONS |
|---|---|---|
| Green dopants | | |
| Iridium(III) organometallic complexes | 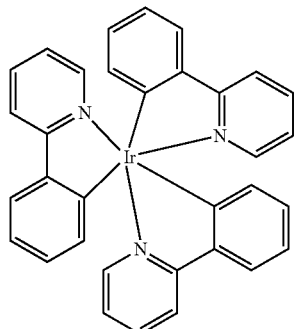<br>and its derivatives | Inorg. Chem. 40, 1704 (2001) |
| | 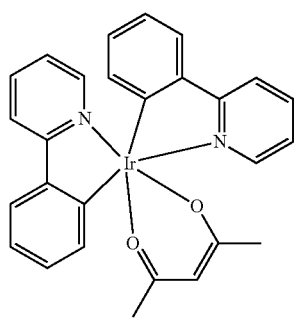 | US2002034656 |
| | 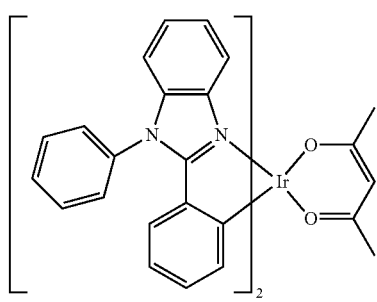 | US06687266 |
| | 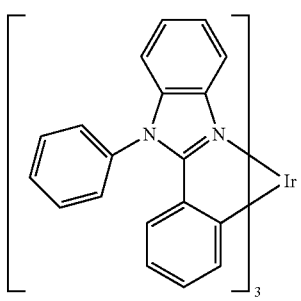 | Chem. Mater. 16, 2480 (2004) |

| MATERIAL | EXAMPLES OF MATERIAL | PUBLICATIONS |
|---|---|---|
| | 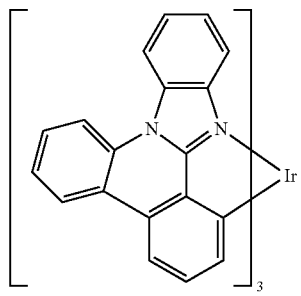 | US2007190359 |
| | 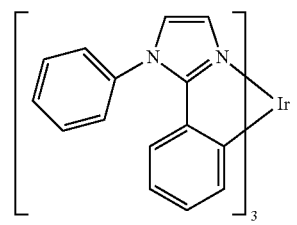 | US 2006008670<br>JP2007123392 |
| | 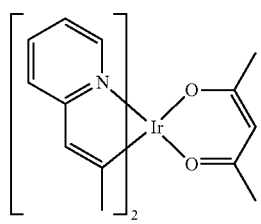 | Adv. Mater.<br>16, 2003<br>(2004) |
| | 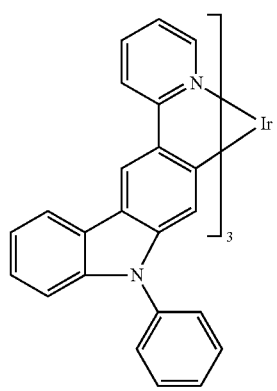 | Angew. Chem.<br>Int. Ed.<br>2006, 45,<br>7800 |
| Pt(II) organometallic complexes | 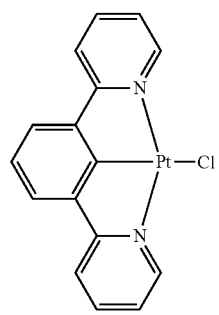 | Appl. Phys.<br>Lett. 86,<br>153505<br>(2005) |

TABLE 1-continued
| MATERIAL | EXAMPLES OF MATERIAL | PUBLICATIONS |
|---|---|---|
| | 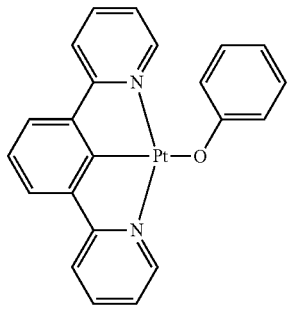 | Appl. Phys. Lett. 86, 153505 (2005) |
| | 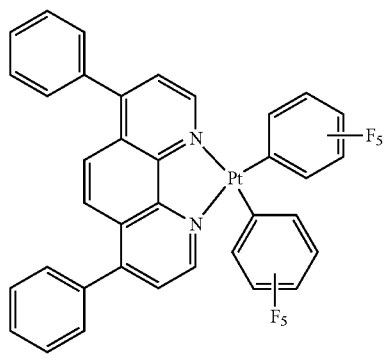 | Chem. Lett. 34, 592 (2005) |
| Gold complexes | 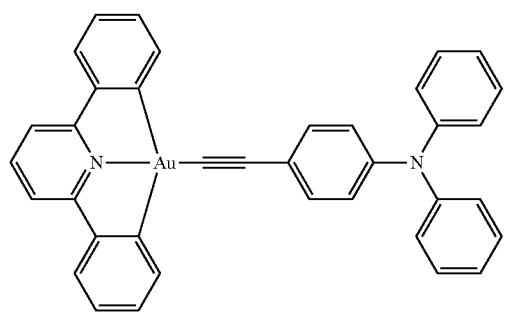 | Chem. Commun. 2906 (2005) |
| Rhenium (III) complexes | 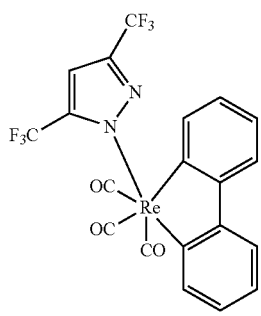 | Inorg. Chem. 42, 1248 (2003) |
Blue dopants

TABLE 1-continued
| MATERIAL | EXAMPLES OF MATERIAL | PUBLICATIONS |
|---|---|---|
| Iridium (III) organometallic complexes | 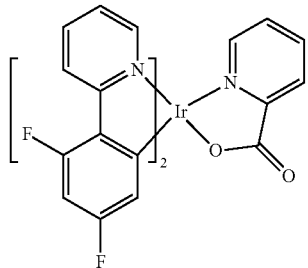 | WO2002002714 |
| | 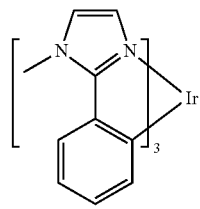 | WO2006009024 |
| | 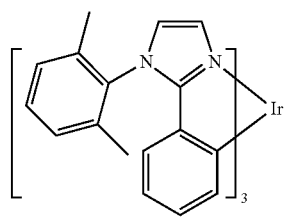 | US2006251923 |
| | 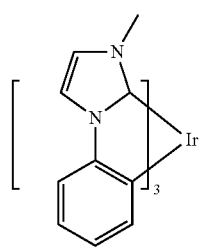 | WO2006056418, US2005260441 |
| | 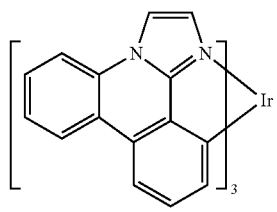 | US2007190359 |
| | 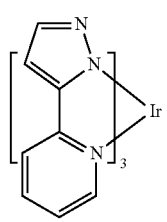 | US2002134984 |

TABLE 1-continued
| MATERIAL | EXAMPLES OF MATERIAL | PUBLICATIONS |
|---|---|---|
| | 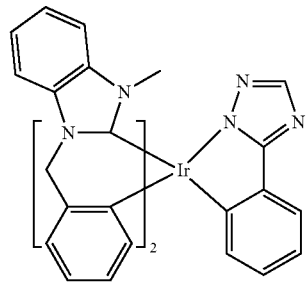 | Angew. Chem. Int. Ed. 47, 1 (2008) |
| | 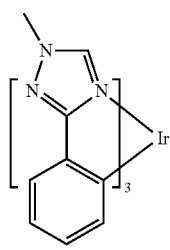 | Chem. Mater. 18, 5119 (2006) |
| | 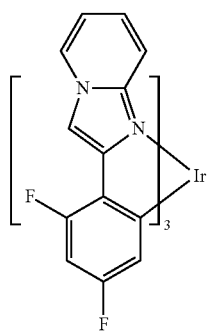 | Inorg. Chem. 46, 4308 (2007) |
| | 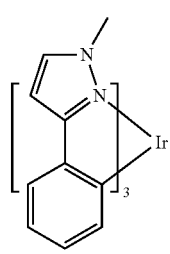 | WO05123873 |
| | 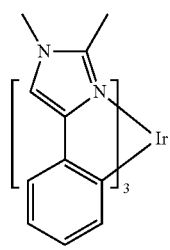 | WO05123873 |

TABLE 1-continued
| MATERIAL | EXAMPLES OF MATERIAL | PUBLICATIONS |
|---|---|---|
| | 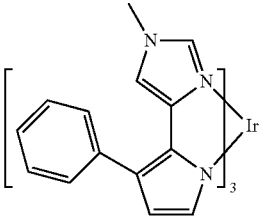 | WO07004380 |
| | 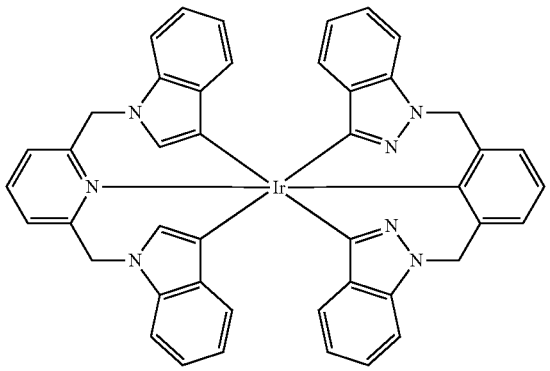 | WO06082742 |
| Osmium (II) complexes | 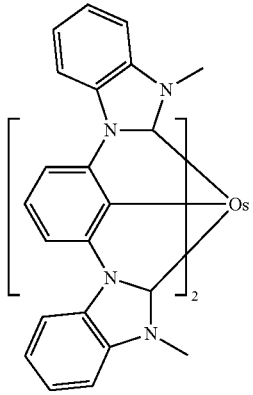 | US2005260449 |
| | 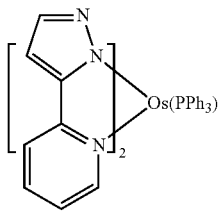 | Organometallics 23, 3745 (2004) |
| Gold complexes | 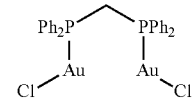 | Appl. Phys. Lett. 74, 1361 (1999) |
| Platinum (II) complexes | 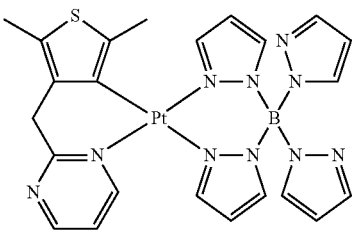 | WO06098120, WO06103874 |

TABLE 1-continued
| MATERIAL | EXAMPLES OF MATERIAL | PUBLICATIONS |
|---|---|---|
| | Exciton/hole blocking layer materials | |
| Bathocuprine compounds (e.g., BCP, BPhen) | 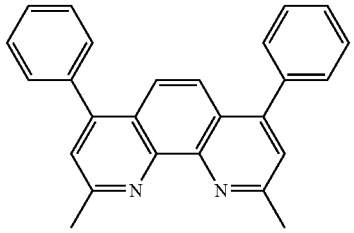 [SMILES: Cc1cc(-c2ccccc2)c2ccc3c(-c4ccccc4)cc(C)nc3c2n1] | Appl. Phys. Lett. 75, 4 (1999) |
| | 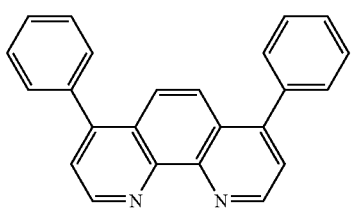 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 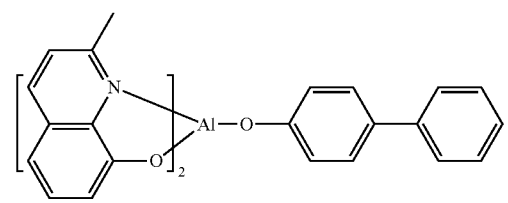 | Appl. Phys. Lett. 81, 162 (2002) |
| 5-member ring electron deficient heterocycles such as triazole, oxadiazole, imidazole, benzoimidazole | 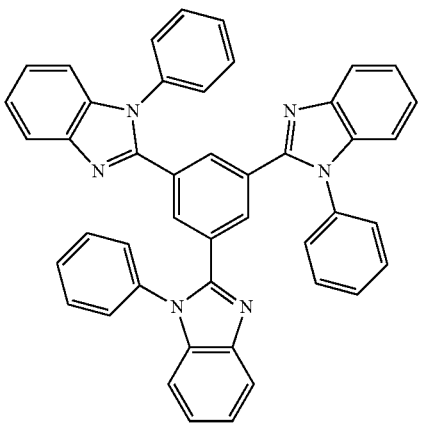 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 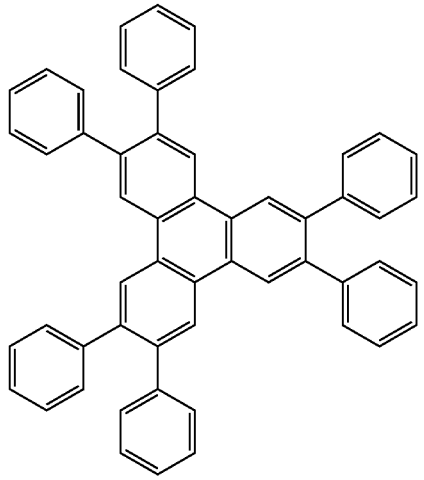 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 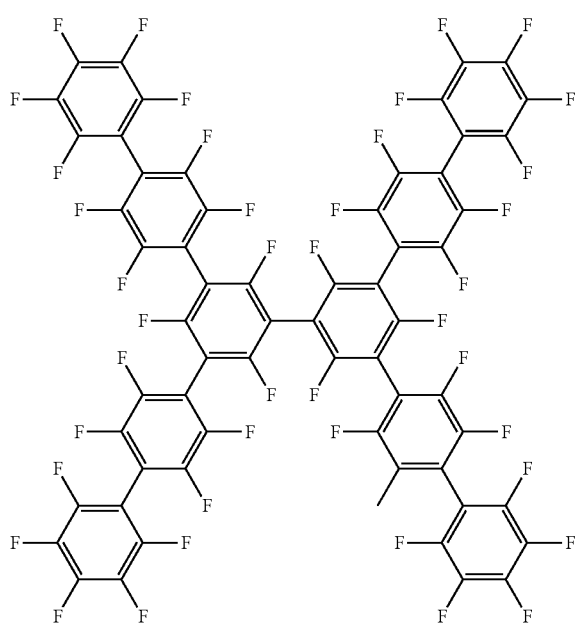 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
Electron transporting materials TABLE 1-continued

| MATERIAL | EXAMPLES OF MATERIAL | PUBLICATIONS |
|---|---|---|
| Anthracene-benzoimidazole compounds | | WO03060956 |
| Anthracene-benzothiazole compounds | | Appl. Phys. Lett. 89, 063504 (2006) |
| Metal 8-hydroxyquinolates (e. g., Alq$_3$) | | Appl. Phys. Lett. 51, 913 (1987) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued

| MATERIAL | EXAMPLES OF MATERIAL | PUBLICATIONS |
|---|---|---|
| 5-member ring electron deficient heterocycles (e. g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

TABLE 1-continued

| MATERIAL | EXAMPLES OF MATERIAL | PUBLICATIONS |
|---|---|---|
| Fluorinated aromatic compounds | 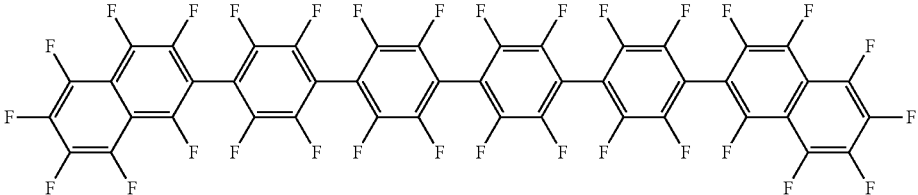 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

EXAMPLES

Synthesis of Example Compounds

The compounds listed in Table 2 were synthesized with the same general procedure as previously reported for unsubstituted BPI (Scheme 1) as described in Siegl, W. O. *J. Org. Chem.* 1977, 42, 1872-1878, Baird, D. M.; Maehlmann, W. P.; Bereman, R. D.; Singh, P. *J. Coord. Chem.* 1997, 42, 107-126, all of which are incorporated by reference.

TABLE 2

The structure of alcohol/ethoxy substituted 1,3-bis(aryl or alkyl)isoindoline dyes.

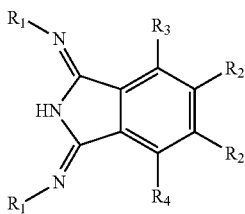

| Complex | R1 | R2 | R3 | R4 |
|---|---|---|---|---|
| 1 | —$C_{12}H_{25}$ | H | OH | OH |
| 2 | (4-tBu-Ph) | H | OH | OH |
| 3 | 2-Pyridyl | H | OH | OH |
| 4 | 2-Pyridyl | Cl | OH | OH |
| 5 | 1-isoquinolyl | H | OH | OH |
| 6 | 2-Pyridyl | H | OEt | OH |

The general synthesis goes as follows: 1 equivalent dicyano species, 2.1 equivalents aryl or alkylamine and 0.1 equivalents $CaCl_2$ were refluxed in butanol or hexanol under $N_2$. After the reaction was discontinued the solvent was either removed by distillation or the reaction mixture poured into water and the precipitate was collected by filtration. After washing with water, the products were then isolated by either column chromatography or precipitation from boiling solvent followed by recrystallization to give the desired products.

1,3-bis(dodecylimino)-4,7-dihydroxyisoindole (1)

A solution of 1.00 g 1,2-dicyanohydroquinone (6.24 mmol), 2.43 g dodecylamine (13.11 mmol) and 0.14 g $CaCl_2$ (1.3 mmol) in 30 ml 1-butanol was refluxed under $N_2$ for 5 days. The reaction mixture was poured into 500 mL of $H_2O$. The precipitate was collected by filtration and was washed with water until no blue fluorescents was observed from the filtrate. The precipitate was then dissolved in boiling methanol and then cooled to 0° C. for 3 days. Precipitate was then collected by filtration and washed with MeOH. 1.1 g (34%), orange solid. Product was further purified by dissolving in $CH_2Cl_2$ and layering with MeOH. MS (Maldi-TOF): m/z=513.91. HRMS-FAB (m/z): [M+H]$^+$ calcd for $C_{32}H_{56}N_3O_2$, 514.4367; found, 514.4376. $^1$H NMR (400 MHz, $CDCl_3$, δ) 6.70 (s, 2H), 3.69 (t, J=6.4 Hz, 4H), 1.76-1.64 (m, 4H), 1.49-1.05 (m, 36H), 0.86 (t, J=6.4 Hz, 6H). $^{13}$C NMR (100 MHz, $CDCl_3$, δ) 173.5, 155.2, 128.5, 113.3, 50.8, 43.3, 31.9, 29.64, 29.62, 29.60, 29.5, 29.3, 29.2, 26.7, 22.7, 14.1.

1,3-bis(p-tert-butyl-phenylimino)-4,7-dihydroxy-isoindole (2)

A solution of 1.00 g 1,2-dicyanohydroquinone (6.24 mmol), 2.09 ml p-tert-butyl-analine (13.11 mmol) and 66 mg $CaCl_2$ (0.62 mmol) in 10 ml 1-hexanol was refluxed under $N_2$ for 2 days. The solvent was removed under reduced pressure and the residue was washed with water. The remaining solid dissolved in methanol and loaded onto silica gel by rotary evaporation. The product was then dry loaded onto a silica gel column and product separated by first eluting with $CH_2Cl_2$ then a 100:1 mixture of $CH_2Cl_2$ and Methanol. The emissive orange fraction was collected and rotary evaporated to dryness. The residue was then dissolved in hot methanol and cooled to −40° C. for two days. The precipitate was collected by filtration. 152 mg (6%), purple powder. MS (Maldi-TOF): m/z=441.75. HRMS-FAB (m/z): [M+H]$^+$ calcd for $C_{28}H_{32}N_3O_2$, 442.2489; found, 442.2483. $^1$H NMR (500 MHz, $CDCl_3$, δ) 7.66 (s, 1H), 7.39 (d, J=7.5 Hz, 4H), 7.02 (d, J=7.5 Hz, 4H), 7.00 (s, 2H), 1.31 (s, 18H).

1,3-bis(2-pyridylimino)-4,7-dihydroxy isoindole (3)

A solution of 1.0 g (6.24 mmol) 2,3-dicyanohydroquinone, 1.23 g (13.11 mmol) 2-aminopyridine and 0.14 g (1.3 mmol) $CaCl_2$ in 20 ml 1-butanol was refluxed under $N_2$. Despite the presents of fluorescent blue 2,3-dicyanohydroquinone starting material, as observed by TLC ($CH_2Cl_2$), the reaction was discontinued after 20 days. The reaction mixture was poured into 500 mL of $H_2O$. The precipitate was collected by filtration and was washed with water until no blue fluorescents was observed from the filtrate. The precipitate was then dissolved in boiling $CH_2Cl_2$ and then cooled to −40° C. overnight. Precipitate was then collected by filtration and washed with MeOH. 0.485 g (24%), yellow needles. MS (Maldi-TOF): m/z=331.85. HRMS-FAB (m/z): $[M+H]^+$ calcd for $C_{18}H_{14}N_5O_2$, 332.1142; found, 332.1136. $^1$H NMR (400 MHz, $CDCl_3$), δ 13.3 (s, 1H), 8.57 (ddd, J=4.8, 2.0, 0.8 Hz, 2H), 7.75 (ddd, J=8.0, 7.6, 2.0 Hz, 2H), 7.35 (d, J=8.0 Hz, 2H), 7.11 (ddd, J=7.6, 4.8, 0.8 Hz, 2H), 7.00 (s, 2H). $^{13}$C NMR (100 MHz, $CDCl_3$) δ 159.3, 154.9, 149.0, 147.9, 147.9, 138.1, 122.4, 121.4, 120.4, 116.2.

5,6-dichloro-1,3-bis(2-pyridylimino)-4,7-dihydroxy-isoindole (4)

A solution of 800 mg (3.5 mmol) 2,3-dichloro-5,6-dicyano-1,4-hydroquinone, 690 mg (7.34 mmol) 2-aminopyridine and 78 mg (0.73 mmol) $CaCl_2$ in 15 ml of 1-hexanol was refluxed under $N_2$ for 2 days. The solvent was removed under reduced pressure. The residue was washed with water until no blue fluorescents was observed from the filtrate. The remaining solid was dissolved in refluxing $CH_2Cl_2$ and filtered while hot. The filtrate was then cooled to 0° C. for 2 days. 254 mg (18%), black needles. MS (Maldi-TOF): m/z=400.06. HRMS-FAB (m/z): $[M+H]^+$ calcd for $C_{18}H_{12}Cl_2N_5O_2$, 400.0363; found, 400.0354. $^1$H NMR (400 MHz, $CDCl_3$), δ 8.55 (d, J=4.8 Hz, 2H), 7.81 (t, J=7.6 Hz, 2H), 7.32 (d, J=7.6 Hz, 2H), 7.18 (t, J=5.6 Hz, 2H).

1,3-bis(1-isoquinolylimino)-4,7-dihydroxyisoindole (5)

A solution of 160 mg (1.0 mmol) 2,3-dicyanohydroquinone, 300 mg (2.08 mmol) 1-aminopyridine and 78 mg (0.73 mmol) $CaCl_2$ in 15 ml of 1-hexanol was refluxed under $N_2$ for 2 days. The solvent was removed under reduced pressure. The residue was washed with water until no blue fluorescents was observed from the filtrate. The remaining solid was dissolved in refluxing $CH_2Cl_2$ and filtered while hot. The filtrate was then cooled to −40° C. for 2 days. 64 mg (15%), green crystalline powder. MS (Maldi-TOF): m/z=431.63. HRMS-FAB (m/z): $[M+H]^+$ calcd for $C_{26}H_{18}N_5O_2$, 432.1455; found, 432.1446. $^1$H NMR (400 MHz, $CDCl_3$), δ 8.62 (d, J=8.4, 2H), 8.53 (d, J=6.0, 2H), 7.84 (d, J=8.4, 2H), 7.75 (t, J=6.8, 2H), 7.68 (t, J=6.8, 2H), 7.53 (d, J=6.0, 2H), 7.10 (s, 2H).

1,3-bis(2-pyridylimino)-4-ethoxy-7-hydroxyisoindole (6)

A solution of 1.17 g (5.43 mmol) 3,6-diethoxyphthalonitrile, 1.28 g (13.6 mmol) 2-aminopyridine and 0.117 g (1.03 mmol) $CaCl_2$ in 17 ml 1-hexanol was refluxed under $N_2$ and monitored for the disappearance of 3,6-diethoxyphthalonitrile by TLC. Upon cooling to room temperature, the solution was poured into 1 L of water and the product was extracted using $CH_2Cl_2$. The organic layer was reduced in volume (50 ml) and the solution was then rotary evaporated onto a silica gel. A silica gel column was then dry loaded with the residue coated silica gel. Fluorescent blue 3,6-diethoxyphthalonitrile starting material was obtained by first eluting with $CH_2Cl_2$. The desired product (fluorescent orange band) was then collected by eluting with $CH_2Cl_2$:MeOH (100:1). Solvent was removed by rotary evaporation and the residue was then dissolved in hot methanol and cooled to 0° C. The precipitate was then collected by filtration. 0.140 g (7%), yellow needles. MS (Maldi-TOF): m/z=360.20. HRMS-FAB (m/z): $[M+H]^+$ calcd for $C_{20}H_{18}N_5O_2$, 360.1455; found, 360.1452. $^1$H NMR (400 MHz, $CDCl_3$), δ 13.8 (s, 1H), 8.60-8.55 (m, 2H), 7.77-7.70 (m, 2H), 7.48 (d, J=8.0, 1H), 7.33 (d, J=8.0, 1H), 7.13-7.06 (m, 2H), 7.05 (s, 1H), 7.04 (s, 1H), 4.28 (q, J=6.8, 2H), 1.55 (t, J=6.8, 3H). $^{13}$C NMR (100 MHz, $CDCl_3$) δ 160.4, 159.3, 155.4, 153.0, 150.4, 149.5, 148.0, 147.5, 138.0, 137.9, 124.1, 122.1, 121.0, 120.6, 120.3, 120.1, 118.8, 66.1, 14.9. Elemental analysis for $C_{20}H_{18}N_5O_2$: calcd: C, 66.84, H, 4.77, N, 19.49. found: C, 67.16, H, 4.65, N, 19.08.

Absorption Properties of Example Compounds

Figure 9:
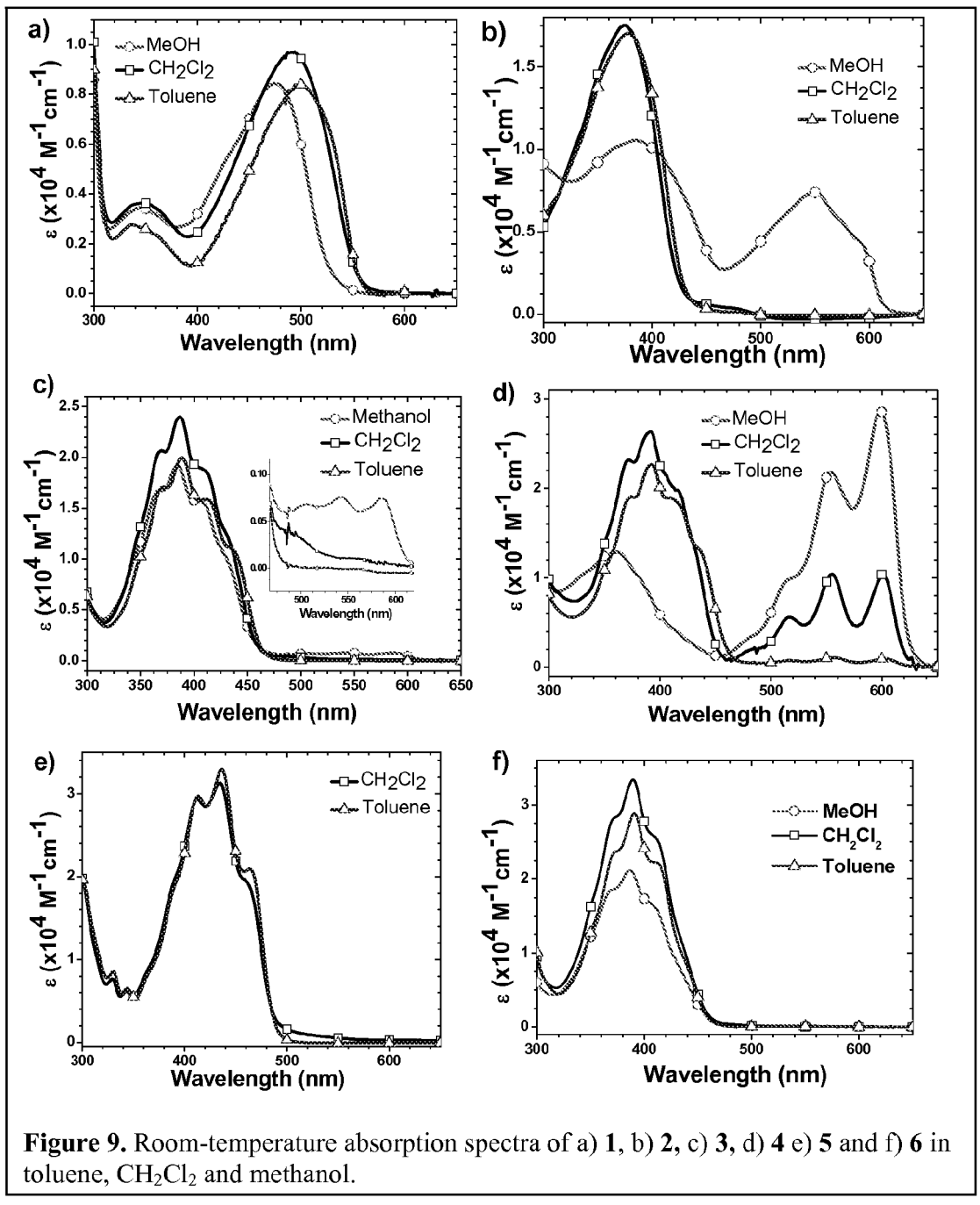
FIG. 9 shows the absorption spectra of Compounds (1)-(6).

The absorption spectra of compounds (1)-(6) are shown in FIG. 9 and the molar absorptivities are summarized in Table 3 below.

TABLE 3

Absorption maxima and molar absorptivity of compounds (1)-(6) in toluene, $CH_2Cl_2$ and methanol

| Molecule | absorbance λ (nm) (ε, ×10$^4$M$^{-1}$cm$^{-1}$) | | |
|---|---|---|---|
| | Toluene | $CH_2Cl_2$ | MeOH |
| 1 | 336(0.24), 499(0.84) | 347(0.36), 492(0.97) | 345(0.34), 472(0.85) |
| 2 | 379(1.71) | 375(1.76) | 384(1.05), 549(0.74), 574(0.56), 593(0.43) |
| 3 | 370(1.70), 388(2.00), 413(1.59), 437(1.09) | 369(2.06), 387(2.40), 413(1.84), 431(1.22) | 366(1.68), 384(1.92), 408(1.56), 543(0.07), 587(0.07) |
| 4 | 401(1.56), 423(2.01), 448(1.54), 436(1.31), 516(0.07), 555(0.11), 603(0.09) | 363(1.29), 478(0.31), 514(0.97), 554(2.18), 599(2.87) | 372(2.32), 392(2.63), 417(1.96), 517(0.56), 555(1.04), 601(1.04) |
| 5 | 330(0.86), 344(0.65), 413(2.97), 436(3.31), 464(2.09) | 329(0.77), 343(0.62), 412(2.93), 434(3.14), 462(1.92) | — |
| 6 | 371(2.36), 391(2.89), 414(2.20) | 371(2.82), 390(3.34), 411(2.55) | 367(1.83), 386(2.11), 410(1.62) |

Emissive Properties of Example Compounds

The emission spectra of compounds (1)-(6) are shown in FIG. 10 and the data are summarized in Table 4 below.

TABLE 4

Photophysical properties of compounds (1)-(6) in various solvents and PMMA.

| Complex | Solvent | emission at rt | | | emission at 77 K$^a$ | |
|---|---|---|---|---|---|---|
| | | $\lambda_{max}$ (nm) | τ (ns) | $\Phi_{PL}$ | $\lambda_{max}$ (nm) | τ (ns) |
| 1 | MeOH | 471, 549 | 6.99, 8.39 | 0.482 | 474 | 8.84 |
| | $CH_2Cl_2$ | 469, 567 | 6.84, 7.89 | 0.061 | | |
| | Toluene | 575 | 7.34 | 0.049 | | |
| | PMMA | 554 | 7.46 | 0.007 | | |
| 2 | MeOH | 600 | 4.14 | 0.121 | 625 | 4.7 |
| | $CH_2Cl_2$ | 604 | 3.71 | 0.023 | | |
| | Toluene | 590 | 3.05 | 0.040 | | |
| | PMMA | 624 | 3.39 | 0.010 | | |
| 3 | MeOH | 592 | 3.67 | 0.305 | 598 | 5.11 |
| | MeOD | 593 | 6.69 | 0.690 | | |
| | $CH_2Cl_2$ | 597 | 3.95 | 0.401 | | |
| | Toluene | 602 | 3.29 | 0.366 | | |
| | PMMA | 593 | 3.56 | 0.25 | | |
| 4 | MeOH | 613 | 4.15 | 0.254 | 622 | 5.99 |
| | $CH_2Cl_2$ | 612 | 4.64 | 0.392 | | |
| | Toluene | 614 | 3.64 | 0.346 | | |

TABLE 4-continued

Photophysical properties of compounds (1)-(6) in various solvents and PMMA.

| Complex | Solvent | emission at rt $\lambda_{max}$ (nm) | emission at rt $\tau$ (ns) | emission at rt $\Phi_{PL}$ | emission at 77 K[a] $\lambda_{max}$ (nm) | emission at 77 K[a] $\tau$ (ns) |
|---|---|---|---|---|---|---|
| 5 | MeOH | 612, 662 | 0.844, 3.97 | 0.036 | 624 | 5.78, 3.15 |
|   | CH$_2$Cl$_2$ | 612, 676 | 0.907, 3.30 | 0.029 | | |
|   | Toluene | 620, 670 | 0.882, 2.67 | 0.044 | | |
| 6 | MeOH | 600 | 3.8 | 0.293 | 620 | 5.27 |
|   | CH$_2$Cl$_2$ | 615 | 4.64 | 0.387 | | |
|   | Toluene | 622 | 4.06 | 0.344 | | |
|   | PMMA | 616 | 4.36 | 0.292 | | |

[a]In 2-MeTHF. All samples recorded in PMMA were at 2% (w/w)

What is claimed is:

1. A compound of the following formula:

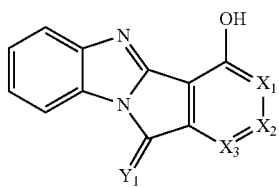

wherein $Y_1$ is $NR_1$; or a compound of the following formula:

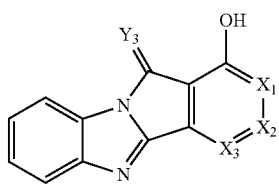

wherein $Y_3$ is $NR_3$, wherein $X_1$, $X_2$, and $X_3$ are independently N or $CR_4$, N or $CR_5$, and N or $CR_6$, respectively, wherein $R_4$ and $R_5$ and/or $R_5$ and $R_6$ can optionally form a ring or $R_4$ and $R_6$ can optionally form a ring, wherein $R_1$, $R_3$, $R_4$, $R_5$, and $R_6$ are independently selected from the group consisting of H, a halogen, a hydroxy group, an amino group, a carboxyl group, an aliphatic group, a heteroaliphatic group, a cyclic group, a heterocyclic group, an aromatic group, a heteroaromatic group, and a combination thereof.

2. A compound selected from the group consisting of the following compounds:

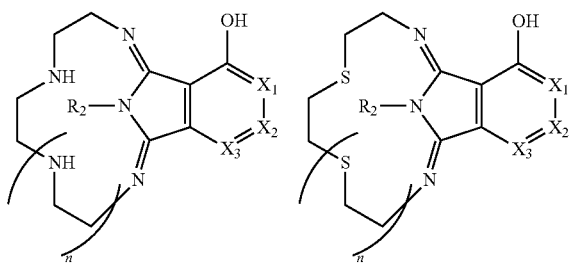

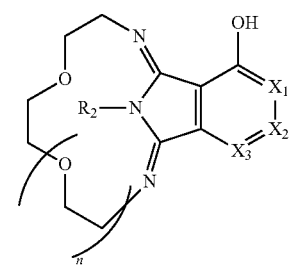

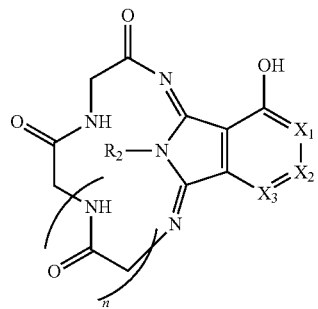

wherein $X_1$, $X_2$, and $X_3$ are independently N or $CR_4$, N or $CR_5$, and N or $CR_6$, respectively, wherein $R_4$ and $R_5$ and/or $R_5$ and $R_6$ can optionally form a ring or $R_4$ and $R_6$ can optionally form a ring, wherein $R_4$, $R_5$, and $R_6$ are independently selected from the group consisting of H, a halogen, a hydroxy group, an amino group, a carboxyl group, an aliphatic group, a heteroaliphatic group, a cyclic group, a heterocyclic group, an aromatic group, a heteroaromatic group, and a combination thereof, wherein n can be any number of repeating units.

3. A complex comprising a metal atom M and a ligand as shown by the following formula:

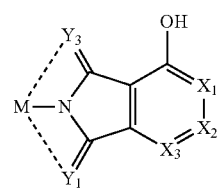

wherein - - - - - represents an optional coordination bond, at least one of which being present, wherein $Y_1$ and $Y_3$ are $NR_1$ and $NR_3$, respectively, at least one containing an atom for forming a coordination bond, wherein $R_1$ and $R_3$ can optionally form a ring, wherein $R_1$ and $R_3$ are the same functional group selected from the group consisting of 2-pyridyl and 1-isoquinolyl, wherein $X_1$ is $CR_4$, $X_2$ is $CR_5$, $R_4$ and $R_5$ being OH or Cl, and wherein $X_3$ is $CR_6$, $R_6$ being OH or OEt.

* * * * *